United States Patent
Burton et al.

(10) Patent No.: US 6,419,624 B1
(45) Date of Patent: Jul. 16, 2002

(54) APPARATUS AND METHOD FOR INSERTING AN ADJUSTABLE IMPLANTABLE GENITOURINARY DEVICE

(75) Inventors: John H. Burton, Minnetonka; Richard A. Noddin, Elk River; Dale L. Schreiner, Cologne; Timothy C. Cook, Wayzata, all of MN (US)

(73) Assignee: Uromedica, Inc., Plymouth, MN (US)

( * ) Notice: Subject to any disclaimer, the term of this patent is extended or adjusted under 35 U.S.C. 154(b) by 0 days.

(21) Appl. No.: 09/415,801

(22) Filed: Oct. 11, 1999

(51) Int. Cl.[7] ................................................. A61F 2/00
(52) U.S. Cl. ................................. 600/29; 128/DIG. 25
(58) Field of Search ............... 600/29–31; 128/DIG. 25

(56) References Cited

U.S. PATENT DOCUMENTS

| | | | |
|---|---|---|---|
| 4,553,959 A | 11/1985 | Hickey et al. | 604/96 |
| 4,559,043 A | 12/1985 | Whitehouse et al. | 604/201 |
| 4,686,962 A | 8/1987 | Haber | |
| 4,773,393 A | 9/1988 | Haber et al. | 600/30 |
| 4,802,479 A | 2/1989 | Haber et al. | 128/344 |
| 4,817,637 A | 4/1989 | Hillegass et al. | 128/899 |
| 4,832,680 A | 5/1989 | Haber et al. | 600/31 |
| 4,846,784 A | 7/1989 | Haber | 600/29 |
| 4,909,785 A | 3/1990 | Burton et al. | 604/54 |
| 4,969,474 A | 11/1990 | Schwarz | 128/885 |
| 5,012,822 A | 5/1991 | Schwarz | 128/885 |
| 5,047,055 A | 9/1991 | Bao et al. | 623/17 |
| 5,064,434 A | 11/1991 | Haber | 623/11 |

(List continued on next page.)

FOREIGN PATENT DOCUMENTS

| | | | | |
|---|---|---|---|---|
| EP | 0784987 A2 | 7/1997 | | |
| EP | 0784987 | 7/1997 | | |
| WO | WO91/00069 | 1/1991 | | |
| WO | 91/00069 | 1/1991 | | |
| WO | 98/20812 | 5/1998 | | A61F/2/06 |
| WO | 98/56311 | 12/1998 | | A61F/2/00 |

OTHER PUBLICATIONS

Lima, S., et al., "Further Experience with the Periurethral Expander: A New Type of Artificial Sphincter", *British Journal of Urology* (1997), 460–462,.

Lima, S. C., et al., "Combined Use of Enterocystoplasty and a new Type of Artificial Sphincter In The Treatment of Urinary Incontinence", *The Journal of Urology, vol. 156*, Aug. 1996, 622–624, (Applicant notes that the attached cover sheets states "Papers Presented at Annual Meeting of the Section on Urology, American Academy of Pediatrics", San Francisco, CA Oct. 14–16, 1995).

*Primary Examiner*—John P. Lacyk
(74) *Attorney, Agent, or Firm*—Schwegman, Lundberg, Woessner & Kluth, P.A.

(57) ABSTRACT

An implantable medical device and method for adjustably restricting a selected body lumen such as a urethra or ureter of a patient to treat urinary incontinence or ureteral reflux. The device includes an adjustable element and a tubular elongate body, where the adjustable element includes a chamber and the tubular elongate body includes at least a first interior passageway which extends longitudinally in the tubular elongate body from a first opening at the proximal end to a second opening in fluid communication with the chamber. Fluid volume passed through the first passageway is used for adjustably expanding or contracting the adjustable element. The implantable medical device further includes a sheath and a sleeve, where the sheath includes a wall having an inner surface which defines a channel through which at least a portion of the implantable device and the sleeve can pass. Alternatively, the implantable medical device includes a tip suitable to penetrate tissue so that the implantable medical device can be implanted within the tissue of a patient.

37 Claims, 25 Drawing Sheets

U.S. PATENT DOCUMENTS

| | | | |
|---|---|---|---|
| 5,097,848 A | 3/1992 | Schwarz | 128/885 |
| 5,112,303 A | 5/1992 | Pudenz et al. | 604/49 |
| 5,123,428 A | 6/1992 | Schwarz | 128/885 |
| 5,133,753 A | 7/1992 | Bark et al. | 623/7 |
| 5,149,052 A | 9/1992 | Stoy et al. | 249/105 |
| 5,181,921 A | 1/1993 | Makita et al. | 606/195 |
| 5,192,326 A | 3/1993 | Bao et al. | 623/17 |
| 5,304,123 A | 4/1994 | Atala et al. | 604/54 |
| 5,334,153 A | 8/1994 | McIntyre et al. | 604/99 |
| 5,336,263 A | 8/1994 | Ersek et al. | |
| 5,376,117 A | 12/1994 | Pinchuk et al. | 623/8 |
| 5,383,896 A | 1/1995 | Gershony et al. | 606/213 |
| 5,385,561 A | 1/1995 | Cerny | 604/264 |
| 5,411,475 A | 5/1995 | Atala et al. | 604/54 |
| 5,437,603 A | 8/1995 | Cerny et al. | 600/29 |
| 5,451,406 A | 9/1995 | Lawin et al. | |
| 5,480,430 A | 1/1996 | Carlisle et al. | 623/7 |
| 5,483,976 A | 1/1996 | McLaughlin et al. | 128/885 |
| 5,496,370 A | 3/1996 | Hamas | 623/11 |
| 5,499,994 A | 3/1996 | Tihon et al. | 606/192 |
| 5,534,023 A | 7/1996 | Henley | 623/8 |
| 5,575,771 A | 11/1996 | Walinsky | 604/96 |
| 5,578,009 A | 11/1996 | Kraus et al. | 604/96 |
| 5,634,877 A | 6/1997 | Salama | 600/29 |
| 5,637,074 A | 6/1997 | Andino et al. | 600/29 |
| 5,830,228 A | 11/1998 | Knapp et al. | 606/195 |
| 5,964,806 A | 10/1999 | Cook et al. | 623/14 |
| 5,976,186 A | 11/1999 | Bao et al. | 623/17 |
| 6,005,020 A | 12/1999 | Loomis | 523/105 |
| 6,033,413 A | 3/2000 | Mikus et al. | 606/108 |
| 6,045,498 A | 4/2000 | Burton et al. | 600/30 |
| 6,120,539 A | 9/2000 | Eldridge | 623/11.11 |
| 6,132,465 A | 10/2000 | Ray et al. | 623/17.16 |

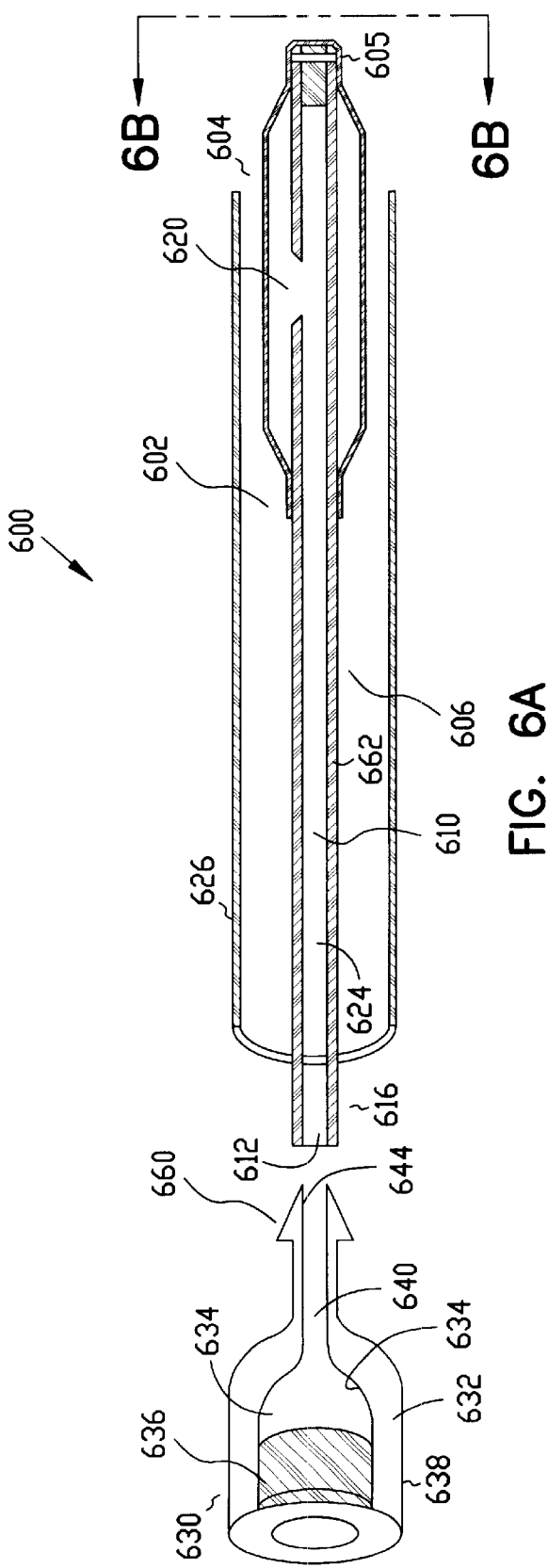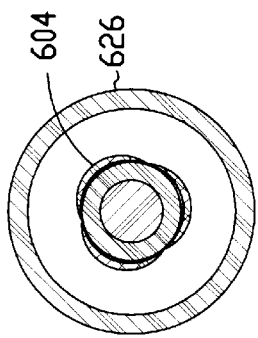
FIG. 6A
FIG. 6B

APPARATUS AND METHOD FOR INSERTING AN ADJUSTABLE IMPLANTABLE GENITOURINARY DEVICE

FIELD OF THE INVENTION

The invention relates generally to implantable medical devices and in particular to implantable medical devices for coaptation of a body lumen.

BACKGROUND OF THE INVENTION

Various implantable devices, such as inflatable/distensible medical devices, are known in which the distensible medical devices are implanted into the tissue of a human to treat urinary incontinence. These devices have typically relied upon restricting or constricting the urethra of the patient to maintain continence.

U.S. Pat. No. 4,733,393 to Haber et al. is an attempt at such a proposed device. U.S. Pat. No. 4,733,393 relates to a hypodermically implantable genitourinary prosthesis which provides an extensible, inflatable tissue expanding membrane to be located in proximal urethral tissue to add bulk to these tissues for overcoming urinary incontinence by localized increase in tissue volume.

U.S. Pat. No. 4,802,479 to Haber et al. is an attempt at an instrument for dispensing and delivering material to an inflatable membrane of a genitourinary prosthesis within the tissues of a patient for overcoming urinary incontinence. U.S. Pat. No. 4,832,680 to Haber et al. relates to an apparatus for hypodermically implanting a genitourinary prosthesis comprising an extensible containment membrane for retaining a fluid or particulate matter which is injected from an external source.

U.S. Pat. No. 5,304,123 to Atala et al. relates to a detachable membrane catheter incorporated into an endoscopic instrument for implantation into the suburethral region of a patient. Also, U.S. Pat. No. 5,411,475 to Atala et al. discusses a directly visualized method for deploying a detachable membrane at a target site in vivo. U.S. Pat. No. 5,830,228 to Knapp et al. relates to a method and system for deployment of a detachable balloon at a target site in vivo.

Once inflated, these devices maintain pressure on the urethra of the patient in an attempt to assist with continence. However, these devices are prone to being under or over inflated at time of implant, leading to undesirable postoperative results. For example, if the devices are overinflated it may cause the urethra to be restricted too tightly, and the patient is at risk for retention, a condition where the patient cannot pass urine. Such a condition could lead to kidney damage, necessitating major corrective surgery or at minimum use of self-catheterization to empty the bladder on a regular basis thus increasing the risk of urinary tract infection.

Furthermore, once these devices have been implanted within the patient, the only means of removing them in the event of a postoperative problem or device malfunction is through major surgery. Also, the devices are not secured within the tissues of the patient, so there is the possibility of the devices migrating back along the pathway created in inserting them, a problem which has been noted with prior art devices. Thus, an important medical need exists for an improved implantable device for treating urinary incontinence.

SUMMARY OF THE INVENTION

The present invention provides an implantable device and a method for its use in restricting a body lumen. In one embodiment, the body lumen is a urethra, where the implantable device is used to coapt the urethra to assist the patient in urinary continence. The implantable medical device has the advantage of being adjustable both at the time of implantation and postoperatively. This postoperative adjustability of the implantable medical device allows a physician to regulate the amount of pressure applied to the urethra to ensure continence of the patient and to minimize iatrogenic effects.

In one embodiment, the present subject matter includes an implantable device assembly for controllable coaptation of a body lumen. The implantable device assembly includes an implantable device which includes an adjustable element and a tubular elongate body. The adjustable element includes a continuous wall, including an inner surface defining a chamber. The tubular elongate body includes a peripheral surface, a proximal end and a distal end, where the peripheral surface is connected to and sealed to the adjustable element. The tubular elongate body further includes at least a first interior passageway which extends longitudinally in the tubular elongate body from a first opening at the proximal end to a second opening in fluid communication with the chamber of the implantable device. This allows for adjustably expanding or contracting the adjustable element by applied flowable material introduced through the first opening. The implantable device assembly also includes a sheath, where the sheath includes a wall having an inner surface which defines a channel through which at least a portion of the implantable device can pass.

In one embodiment, the implanted device is inserted into body tissue by passing the device through the sheath. The sheath is first inserted into the tissue of the patient and then the implanted device is moved through the channel of the sheath. In one embodiment, the implanted device is moved through the sheath through the use of a push rod, where the push rod is inserted into the first interior passageway. As the push rod is inserted into the first interior passage way it comes into contact with a closed end distal to both the first opening and second opening of the first interior passage way. Force can then be applied to the push rod to move the implanted device at least partially through the channel of the sheath.

In an alternative embodiment, the tubular elongate body includes a second interior passageway which extends longitudinally along at least a portion of the tubular elongate body from an inlet to a closed end. The second interior passageway is of sufficient diameter to receive the push rod which contacts the closed end to allow force applied to the push rod to move the implanted device at least partially through the channel of the sheath.

In an additional embodiment, the implantable device assembly can further include a sleeve having a longitudinal slot, where at least a portion of the implanted device is housed in the volume defined by the sleeve. In one embodiment, the sleeve and implanted device are passed through the sheath so as to extend the adjustable element past the distal end of the sheath. The adjustable element is then expanded so that contact is made with the tissue. In one embodiment, the sheath is withdrawn from the body, after which the sleeve is then either passed around a portion of the implanted device or a portion of the implanted device deforms to allow the implanted device to pass through the sleeve. In an alternative embodiment, the sleeve is withdrawn from the body, after which the sheath is passed around a portion of the implanted device.

In an additional embodiment, the implantable device includes a rear port element coupled to the proximal end of the tubular elongate body. In one embodiment, the rear port element is releasably attached to the tubular elongate body. The rear port element including a cavity in fluid communication with the first opening of the first interior passageway. This allows for fluid volume passed through the rear port element to either expand or contract the size of the adjustable element. In one embodiment, the rear port element has an elastic septum to receive a needle through which flowable material can pass to expand or contract the adjustable element.

The sheath of the present subject matter also includes a first portion and at least one of a second portion, where the second portion is of a lesser strength compared to the first portion. In one embodiment, the second portion extends longitudinally along the wall to allow for the wall of the sheath to be separated. In one embodiment, the second portion of the wall includes scorings extending longitudinally along the wall which create a weak area over which the sheath can be torn. In an additional embodiment, the wall of the sheath can include two scorings extending longitudinally along the wall to allow for the sheath to be separated into two pieces. Alternatively, the sheath can include a slit through the wall, where the slit extends longitudinally along the wall.

In an additional embodiment, the implanted device further includes a tip suitable to penetrate tissue. In one embodiment, the tip is positioned, or is formed, at the distal end of the tubular elongate body. Alternatively, the distal end of the push rod forms the tip, where the tip is exposed at the distal end of the tubular elongate body when the distal end of the push rod passes through an outlet end in the second interior passage way.

Finally, an important feature of the implantable device of the present invention relates to the adjustable element or membrane which is accessible for subsequent adjustment in volume through the rear port element located under a patient's skin, remotely from the adjustable element. Another important feature of the present invention over the prior art devices is the convenient in vivo postoperative adjustability of both pressure and size of the adjustable element.

BRIEF DESCRIPTION OF THE DRAWINGS

FIG. 6A is a schematic cross-sectional view of the implantable device assembly according to one embodiment of the present subject matter;

FIG. 6B is a schematic end view of the implantable device assembly according to one embodiment of the present subject matter;

DETAILED DESCRIPTION OF THE INVENTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that logical, and structural changes may be made without departing from the spirit and scope of the present invention. The following detailed description is, therefore, not to be taken in a limiting sense and the scope of the present invention is defined by the appended claims and their equivalents.

The present subject matter describes embodiments of an implantable device assembly and/or an implantable device for restricting a body lumen. In one embodiment, the present subject matter is for treating urinary incontinence by implanting at least one of the implantable devices adjacent the urethra. In an alternative embodiment, the present subject matter is for treating ureteral reflux of a patient by implanting at least one of the implantable devices adjacent one or both ureter proper. Additionally, the present subject matter is useful in treating urinary stress incontinence resulting from male post radical prostatectomy, esophageal reflux, fecal incontinence or vascular restriction.

Implantable devices designed for treating urinary incontinence are typically referred to as a genitourinary prosthesis. Many designs for genitourinary prosthesis have been proposed. In one such proposed embodiment, the genitourinary prosthesis comprises an implantable device which includes a rear port element coupled to a tubular elongate body and an adjustable element, where the adjustable element has a chamber designed to receive a measured supply of flowable material introduced through the rear port element to inflate the prosthesis. One such description of a genitourinary prosthesis is also provided in a U.S. patent application Ser. No. 08/928946, entitled "ADJUSTABLE IMPLANTABLE GENITOURINARY DEVICE" filed Sep. 12, 1997, by Burton et al., which is hereby incorporated by reference in its entirety.

In treating urinary incontinence, the prosthesis is delivered within the body to a location that is typically within the periurethral tissue and adjacent to the urethra to enable a patient to overcome urinary incontinence by means of increasing both localized tissue volume and passive occlusive pressure upon the urethral mucosa. The implantable device of the present subject matter is useful for accomplishing this objective, while the implantable device assembly of the present subject matter is useful in delivering the implantable device to a desired location within the body of the patient.

Figure 1:
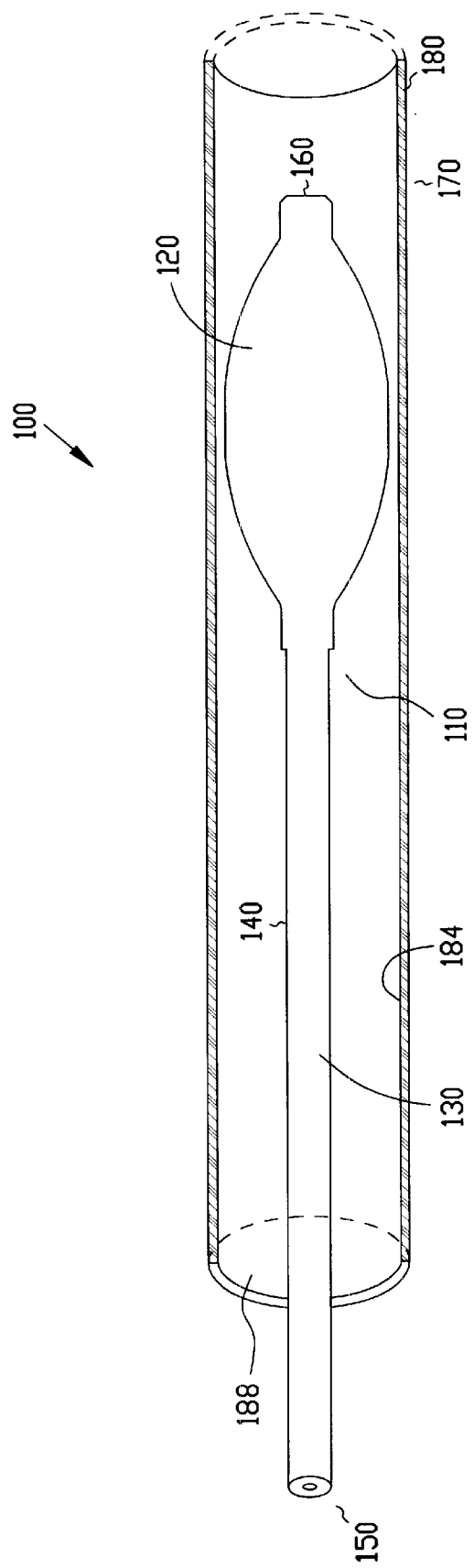
FIG. 1 is a schematic view of an implantable device assembly according to one embodiment of the present subject matter, where a sheath is shown in cross-sectional view to reveal an implantable device.

Referring now to FIG. 1, there is shown one embodiment of an implantable device assembly 100 according to the present subject matter. In one embodiment, the implantable device assembly is for delivering into a body an implantable device 110 for the controllable coaptation, or restriction, of a body lumen. In one embodiment, the implantable device 110 is for treating ureteral reflux of a patient by implanting at least one of the implantable device 110 adjacent one or both ureter proper. In an alternative embodiment, the implantable device 110 is for treating urinary incontinence by implanting at least one of the implantable device 110 adjacent the urethra.

In FIG. 1, the implantable device 110 is shown to include an adjustable element 120 and a tubular elongate body 130. In one embodiment, the adjustable element 120 includes a continuous wall, including an inner surface defining a chamber. The tubular elongate body 130 includes a peripheral surface 140, a proximal end 150 and a distal end 160, where the peripheral surface 140 is connected to and sealed to the adjustable element 120. The implantable device 110 is shown positioned within a sheath 170, where the sheath 170 includes a wall 180 having an inner surface 184 which defines a channel 188 through which at least a portion of the implantable device 110 can pass. In the embodiment shown in FIG. 1, a cross sectional view of the sheath 170 is shown so as to reveal the implantable device 110 positioned at least partially within the channel 188.

Figure 2:
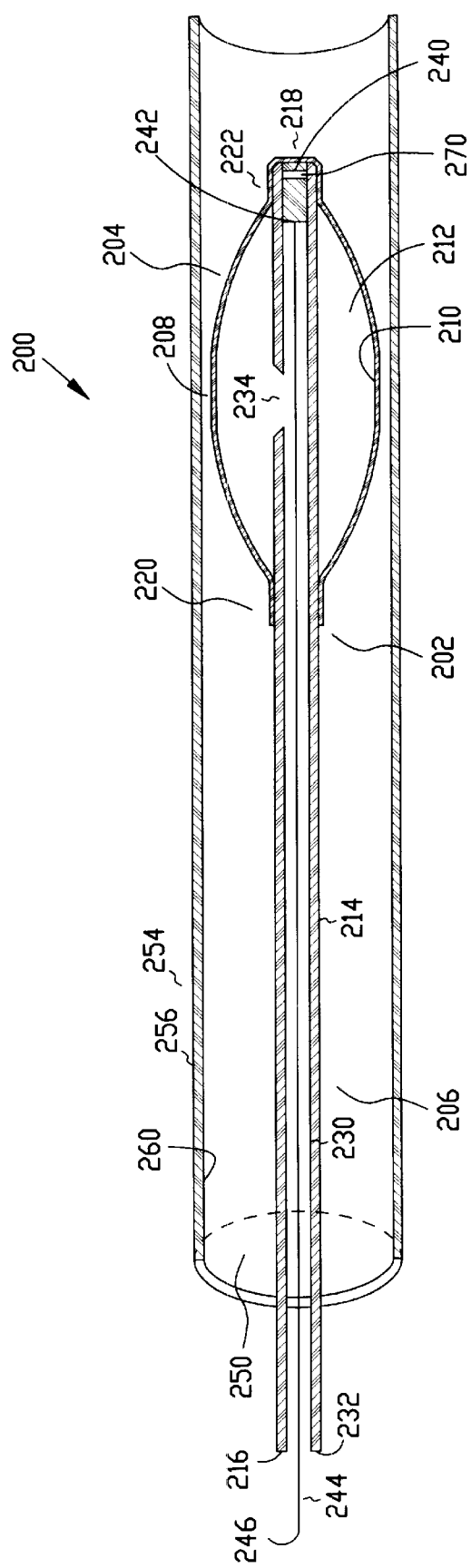
FIG. 2 is a schematic cross-sectional view of the implantable device assembly according to one embodiment of the present subject matter.

Referring now to FIG. 2, there is shown a schematic cross-sectional view of the implantable device assembly 200 according to one embodiment of the present subject matter. An implantable device 202 is shown to include an adjustable element 204 and a tubular elongate body 206. In one embodiment, the adjustable element 204 includes a continuous wall 208, including an inner surface 210 defining a chamber 212. The tubular elongate body 206 includes a peripheral surface 214, a proximal end 216 and a distal end 218. The adjustable element 204 has at least one opening through the continuous wall 208 to which the peripheral surface 214 is connected to and sealed to the adjustable element 204.

In one embodiment, a first portion 220 and a second portion 222 of the inner surface 210 of the adjustable element 204 and the peripheral surface 214 are sealed using a chemical or polymer adhesive, such as silicone. In an alternative embodiment, the peripheral surface 214 is sealed to the first portion 220 and the second portion 222 using sonic welding techniques as are known in the art. The final result of bonding the first portion 220 and the second portion 222 of the inner surface 210 of the adjustable element 204 to the peripheral surface 214 of the tubular elongate body 206 is that a fluid tight bond or seal is created between the inner surface 210 of the adjustable element 204 and the peripheral surface 214 of the tubular elongate body 206.

In one embodiment, the tubular elongate body 206 includes at least a first interior passageway 230 which extends longitudinally in the tubular elongate body 206 from a first opening 232 at the proximal end 216 to a second opening 234. In one embodiment, the second opening 234 is in fluid communication with the chamber 212 of the implantable device for adjustably expanding or contracting the adjustable element 204 by flowable material introduced through the first opening 232. In one embodiment, the fluid tight bonding at the first portion 220 and the second portion 222 allows for the chamber 212 to maintain pressure provided by the flowable material so that the size of the adjustable element 204 can be changed.

In one embodiment, the adjustable element 204 is constructed of a biocompatible resiliently elastomeric polymer or polymer blend of polyurethane, silicone, or the like. In this embodiment, the wall 208 stretches as the adjustable element 204 expands or contracts to a desired size. In an alternative embodiment, the continuous wall 208 is constructed of a biocompatible non-resilient polymer or polymer blend of polyethylene, polyethyleneterephthalate (PET), polyurethane, high modulus polystyrene, polyesteretherketone (PEEK), or other nonresilient polymers as known. In this embodiment, the continuous wall 208 of the adjustable element 204 expand to a predetermined shape. The adjustable element 204 is formed into a variety of shapes. In one embodiment, the outer surface of the continuous wall 208 generally defines a spherical shape. In an alternative embodiment, the outer surface of the continuous wall 208 generally defines an elongate body having semi-spherical end portions.

In one embodiment, the continuous wall 208 of the adjustable element 204 has a length and a diameter when inflated to operating volume, where the dimension of the length and diameter are selected in a range from one-half (0.5) centimeter to five (5) centimeters, where each of the length and diameter are selected independently. Alternatively, the adjustable element 204 can have a length and a diameter that are equal (length=diameter) so as to give a generally spherical shape to the adjustable element. In one embodiment, the adjustable element 204 has a spherical shape with a length and diameter of up to three (3) centimeters. In an alternative embodiment, the adjustable element 204 has a spherical shape with a length and diameter of up to one and one-half (1.5) centimeters.

Other configurations of length and diameter are possible so as to give adjustable elements 204 of different shapes. For example, the adjustable element can have an elliptical or kidney cross-sectional shape to facilitate at least partially surrounding the body lumen with the adjustable element, where the adjustable element is concave relative to the urethral lumen. The dimensions discussed for the adjustable element apply to all embodiments of the present subject matter.

In one embodiment, the first interior passageway 230 includes a closed end 240, where the closed end 240 is positioned distal to both the first opening 232 and second opening 234. The closed end 240 is of sufficient strength and hardness to receive a distal end 242 of a push rod 244, where the closed end 240 transfers force applied at a proximal end 246 of the push rod 244 to the implantable device 202.

In one embodiment, the first interior passageway 230 is of sufficient diameter to receive the push rod 244 which contacts the closed end 240 to allow force applied to the push rod 244 to move the implanted device 202 at least partially through a channel 250 of a sheath 254. In one embodiment, the implantable device 202 is shown positioned within the sheath 254, where the sheath 254 includes a wall 256 having an inner surface 260 which defines the channel 250 through which at least a portion of the implantable device 202 can pass.

In one embodiment, the push rod 244 has a length between a first end an a second end of the push rod in a range of ten (10) to forty (40) centimeters, a diameter of between 0.05 to 0.16 centimeters, where the diameter of the push rod will depend upon the construction material for the rod. In one embodiment, the push rod is made of stainless steel. Alternatively, the push rod is made of a plastic. In an additional embodiment, the push rod is made of a material having a yield strength greater than 12,000 psi.

In an additional embodiment, a detectable marker is imbedded in the implantable device 202. For example, the detectable marker 270 is located at the distal end 218, (e.g., the tip) of the tubular elongate body 206. Alternatively, the detectable marker could be located in the continuous wall 208 of the adjustable element 204. The detectable marker 270 allows the adjustable element 204 to be located and its shape to be visualized within the tissues of a patient using any number of visualization techniques which employ electromagnetic energy as a means of locating objects within the body. In one embodiment, the detectable marker 270 is constructed of tantalum and the visualization techniques used to visualize the adjustable element 204 are x-ray or fluoroscopy as are known in the art. In an additional embodiment, the sheath could also have a detectable marker, where the marker could be incorporated into, or on, the wall of the sheath. Alternatively, the entire sheath could be constructed so as to be radio opaque.

Figure 3:
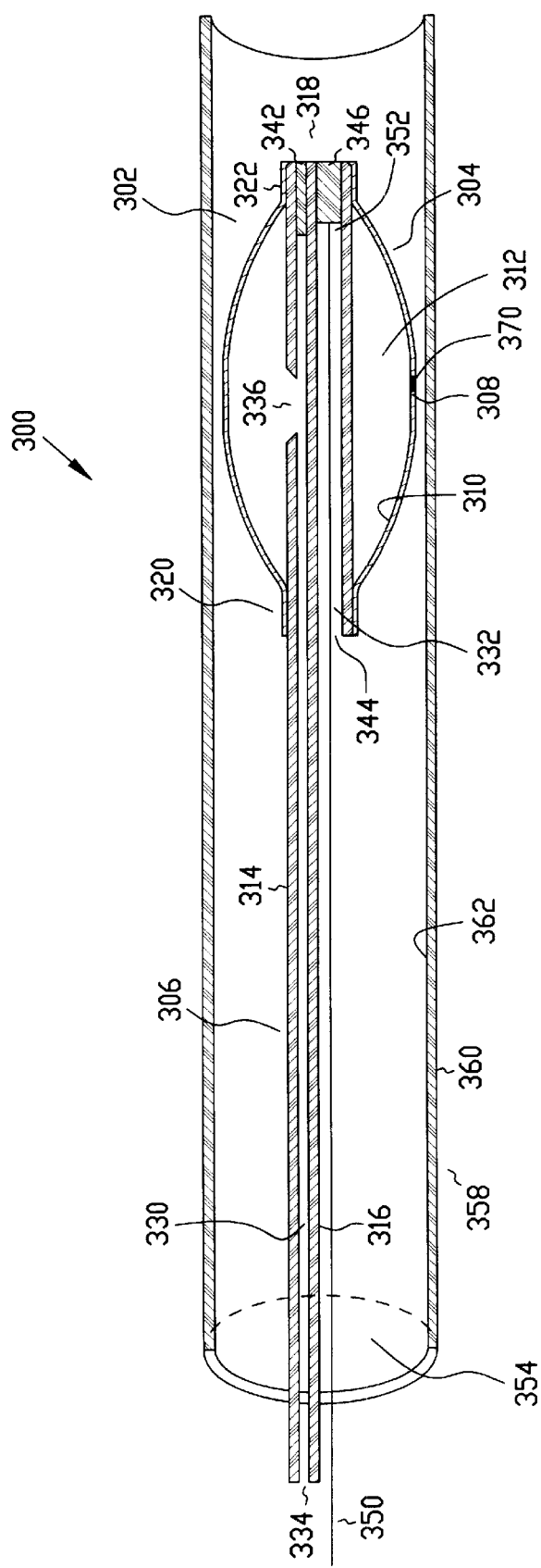
FIG. 3 is a schematic cross-sectional view of the implantable device assembly according to one embodiment of the present subject matter.

Referring now to FIG. 3, there is shown a schematic cross-sectional view of an implantable device assembly 300 according to one embodiment of the present subject matter. The implantable device assembly 300 is shown to include an implantable device 302. The implantable device 302 includes an adjustable element 304 and a tubular elongate body 306. In one embodiment, the adjustable element 304 includes a continuous wall 308, including an inner surface 310 defining a chamber 312. The tubular elongate body 306 includes a peripheral surface 314, a proximal end 316 and a distal end 318. In one embodiment, the peripheral surface 314 is connected to and sealed to the adjustable element 304.

In one embodiment, a first portion 320 and a second portion 322 of the inner surface 310 of the adjustable element 304 is chemically bonded to the peripheral surface 314 of the tubular elongate body 306. Alternatively, the first portion 320 and/or the second portion 322 of the inner surface 310 of the adjustable element 304 is mechanically and/or thermally welded to the peripheral surface 314 of the tubular elongate body 306. The final result of bonding the first portion 320 and the second portion 322 of the inner surface 310 of the adjustable element 304 to the peripheral surface 314 of the tubular elongate body 306 is that a fluid tight bond or seal is created between the inner surface 310 of the adjustable element 304 and the peripheral surface 314 of the tubular elongate body 306.

In one embodiment, the tubular elongate body 306 includes a first interior passageway 330 and a second interior passageway 332. In one embodiment, the first interior passageway 330 extends longitudinally in the tubular elongate body 306 from a first opening 334 at the proximal end 316 to a second opening 336. In one embodiment, the second opening 336 is in fluid communication with the chamber 312 of the implantable device for adjustably expanding or contracting the adjustable element 304 by flowable material introduced through the first opening 334. In one embodiment, the fluid tight bonding at the first portion 320 and the second portion 322 allows for the chamber 312 to maintain volume provided by the flowable material so that the size of the adjustable element 304 can be changed. In one embodiment, the first interior passageway 330 includes a closed end 342, where the closed end 342 is positioned distal to both the first opening 334 and second opening 336.

In one embodiment, the second interior passageway 332 extends longitudinally along at least a portion of the tubular elongate body 306 from an inlet 344 to a closed end 346. In one embodiment, the second interior passageway 332 is of sufficient diameter to receive a push rod 350 which contacts the closed end 346 to allow force applied to the push rod 350 to move the implanted device 302 at least partially through a channel 354 of a sheath 358. In one embodiment, the closed end 346 is of sufficient strength and hardness to receive a distal end 352 of the push rod 350, where the closed end 346 transfers force applied at a proximal end 354 of the push rod 350 to the implantable device 302. In one embodiment, the force applied to the push rod 350 moves the implanted device 302 at least partially through the channel 354 of the sheath 358. In one embodiment, the implantable device 302 is shown positioned within the sheath 358, where the sheath 358 includes a wall 360 having an inner surface 362 which defines the channel 354 through which at least a portion of the implantable device 302 can pass.

In one embodiment, the second interior passageway 332 forms a portion of the tubular elongate body and extends from the inlet located at the proximal end 316 of the tubular elongate body 306 to the closed end 346 located at or proximal to the distal end 318 of the tubular elongate body 306. Alternatively, the second interior passageway 332 extends longitudinally within the tubular elongate body 306 for only a portion of the overall length of the tubular elongate body 306, as is shown in FIG. 3.

In an additional embodiment, a detectable marker is imbedded in the implantable device 302. For example, the detectable marker 370 is located at the distal end 318, (e.g., the tip) of the tubular elongate body 306. Alternatively, the detectable marker could be located in the continuous wall 308 of the adjustable element 304. The detectable marker 370 allows the adjustable element 304 to be located and its shape to be visualized within the tissues of a patient using any number of visualization techniques which employ electromagnetic energy as a means of locating objects within the body. In one embodiment, the detectable marker 370 is constructed of tantalum and the visualization techniques used to visualize the adjustable element 304 are x-ray or fluoroscopy as are known in the art. In an additional embodiment, the sheath could also have a detectable marker, where the marker could be incorporated into, or on, the wall of the sheath. Alternatively, the entire sheath could be constructed so as to be radio opaque.

Figure 4A:
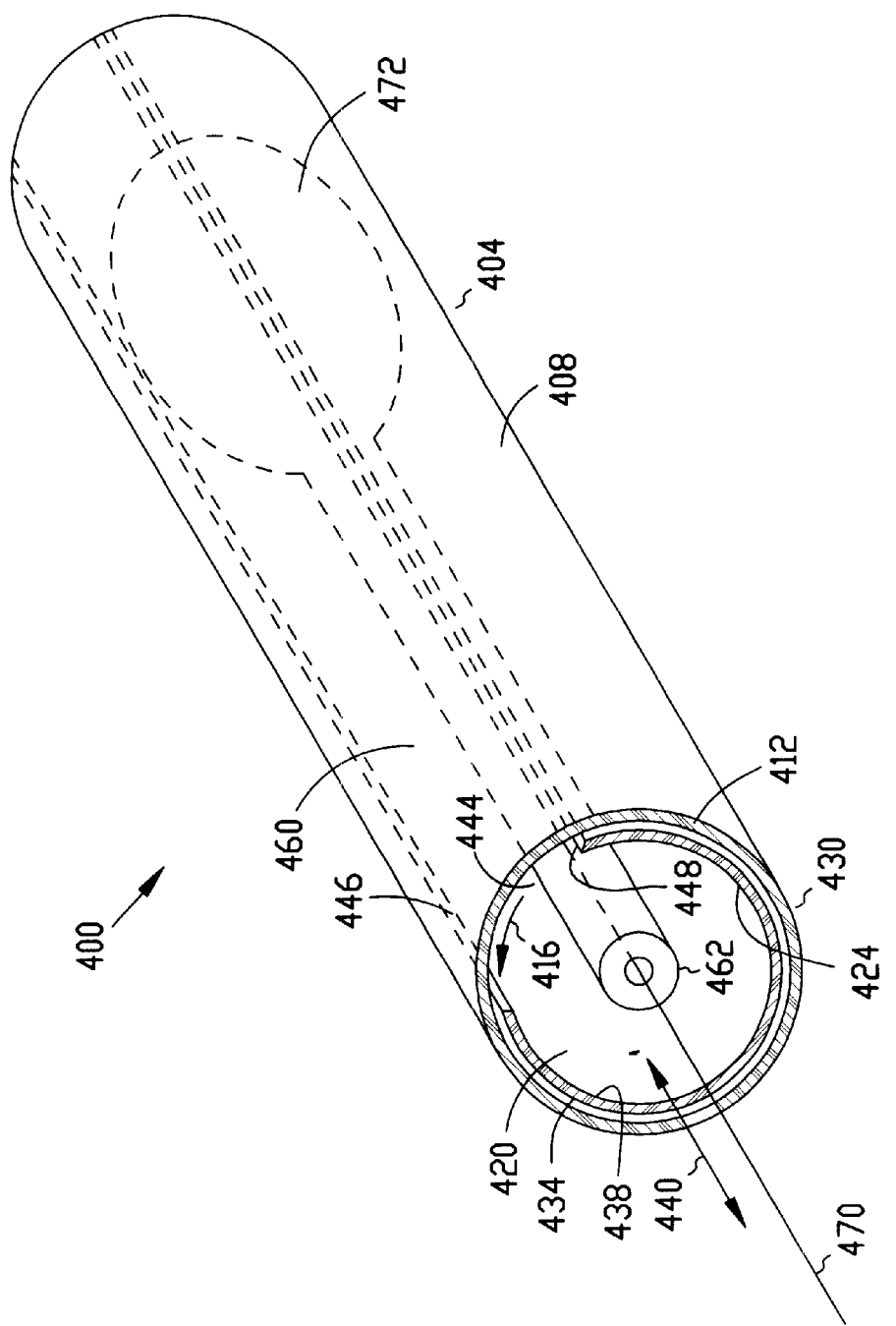
FIG. 4A is a schematic of the implantable device assembly according to one embodiment of the present subject matter.

Referring now to FIG. 4A, there is shown a schematic of an implantable device assembly 400 according to one embodiment of the present subject matter. The present implantable device assembly 400 includes a sheath 404, where the sheath 404 includes an elongate body 408 having a wall 412. The wall 412 includes an inner surface 416 which defines a channel 420. Included within the channel 420 is a sleeve 424. The sleeve 424 includes a wall 430 having an outer surface 434 and an inner surface 438. In one embodiment, the outer surface 434 and the inner surface 438 define an arc, or a partial cylinder or curved portion, of the wall 430. In one embodiment, the arc of the wall 430 has a first dimension, such as a radius of curvature, with respect to the outer surface 434 of the wall 430 which permits the sleeve 424 to be positioned within the channel 420 of the sheath 404. In addition, the first dimension of the sleeve is of a size which permits the sleeve 424 to move longitudinally within the channel 420 of the sheath 404 as is shown by arrow 440.

In one embodiment, the sleeve 424 includes a channel 444 between a first edge 446 and a second edge 448 on the wall 430 of the sleeve 424. In one embodiment, the first edge 446 and the second edge 448 of the channel 444 are parallel and extend longitudinally along the length of the sleeve 424. Alternatively, the first edge 446 and the second edge 448 of the channel 444 converge or diverge, or both, longitudinally along the length of the sleeve 424. The inner surface 438 of the sleeve 424 includes a second dimension, that is smaller than the first dimension of the outer surface, where the second dimension allows for a volume 460 to be defined. In one embodiment, the second dimension is of a radius for the inner surface of the arc defined by the wall 430. The volume 460 is of sufficient size to permit the tubular elongate body and the adjustable element of the implantable device 462 to fit in the volume 460 defined by inner surface 438 of the sleeve 424. In one embodiment, the implantable device 462 is of the type previously described.

The implantable device 462 is placed in the volume 460 defined by the sleeve 424 and the sleeve 424 and the implantable device 462 are then inserted into the channel 420 of the sheath 404. Once inside the sheath 404, the implantable device 462 and the sleeve 424 are advanced through the sheath 404 by applying force to either the sleeve 424 or to the implantable device 462. In one embodiment, force applied to the sleeve 424 is provided by pushing or pulling at one or more points along the wall 430 of the sleeve 424. When positioned in the sleeve 424 and the sheath 404, the implantable device 462 has sufficient contact with the wall 430 of the sleeve 424 to prevent the adjustable member 472 of the implantable device 462 from slipping along the wall 430. In other words, the dimensions of the outer surface of the adjustable member 472 and the inner surface 438 of the sleeve 424 provide for frictional forces sufficient to prevent the implantable device 462 to move relative to the sleeve 424 as the sleeve and implantable device are moved through the sheath.

Figure 4B:
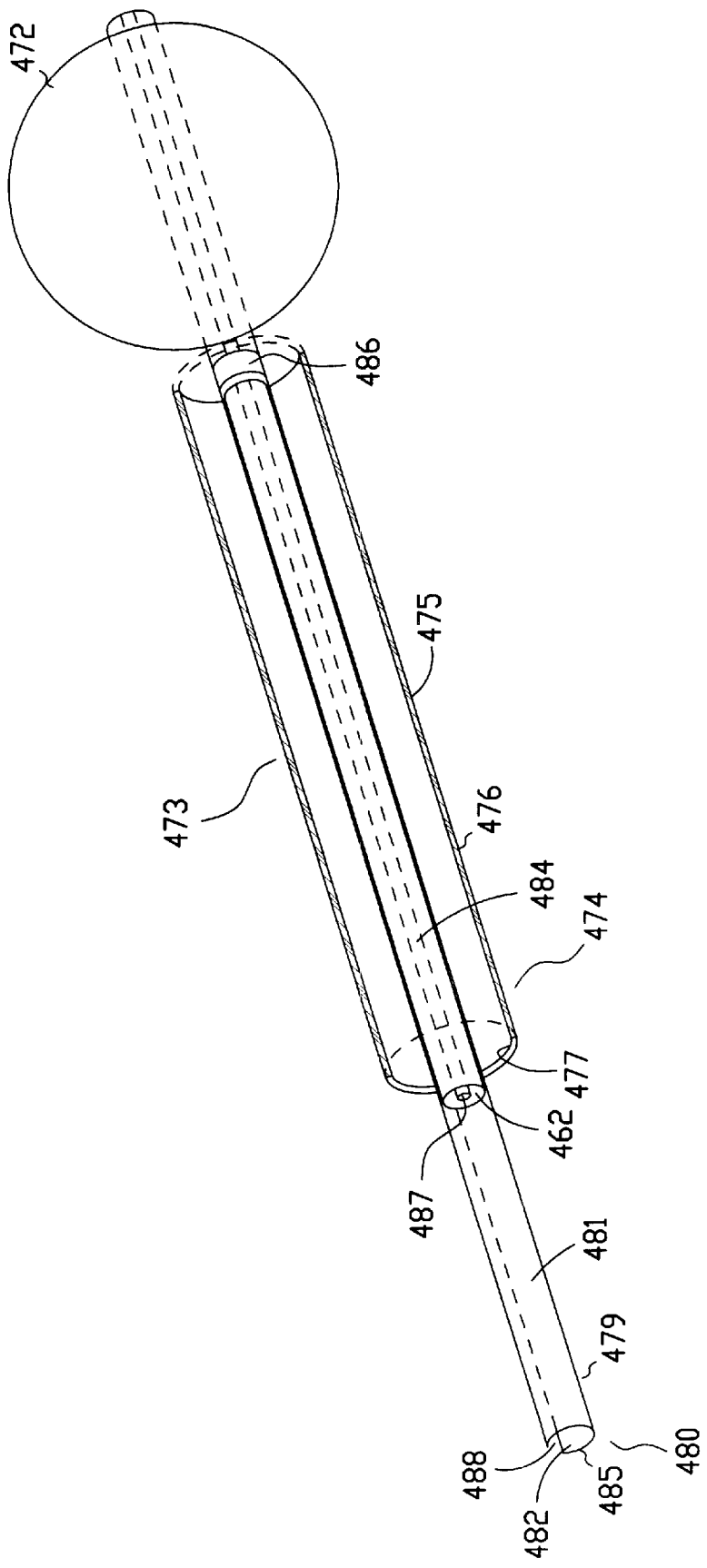
FIG. 4B is a schematic of the implantable device assembly according to one embodiment of the present subject matter.

Referring now to FIG. 4B there is shown an alternative embodiment of an implantable device assembly 473 according to one embodiment of the present subject matter. The present implantable device assembly 473 includes a sheath 474, where the sheath 474 includes an elongate body 475 having a wall 476. The wall 476 includes an inner surface 477 which defines a channel 478. The implantable device assembly 473 further includes a sleeve 479. The sleeve 479 includes a wall 480 having an outer surface 481 and an inner surface 482. In one embodiment, the outer surface 481 and the inner surface 482 define an arc, or a partial cylinder or curved portion, of the wall 480. In one embodiment, the arc of the wall 480 has a an inner diameter with respect to the inner surface 482 of the wall 480 which permits the sleeve 479 to be positioned around the peripheral surface 483 of the tubular elongate body 484 of the implantable device 462. The sleeve 479 also includes a proximal end 484 and a distal end 485, where the distal end abuts a ridge, or ledge, formed at the point where the peripheral surface 483 of the tubular elongate body is connected to and sealed to the adjustable element 472.

The sleeve 479 allows for the implantable device 462 to be advanced through the sheath 474 by force applied at the distal end 485 of the sleeve 479. Once the adjustable element 472 has been advanced past the distal end of the sheath 474, the adjustable element 472 can be expanded (as shown) to fix the position of the implantable device 462 in the tissue of a patient. The adjustable element 472 is expanded by fluid volume introduced into the first interior passageway 487. In one embodiment, once expanded, the sheath 474 is withdrawn from the body. The sleeve 479 is then either pulled, or slid, off the tubular elongate body 484, or the tubular elongate body 484 is passed through the slot 488 of the sleeve 479. Alternatively, once expanded, the sleeve is either pulled, or slid, off the tubular elongate body 484 or the tubular elongate body 484 is passed through the slot 488 of the sleeve 479. The sheath 474 is then withdrawn from the body.

In one embodiment, the sleeve 479 has an inner diameter that is between zero (0) to five (5) percent larger than the diameter of the tubular elongate body 484. Additionally, the sheath, as described in any of the present embodiments, has an inner diameter that is in a range of between 1.27 to 3.81 millimeters (or 0.050 inches to 0.150 inches). In one embodiment, the outer diameter of the sheath, as described in any of the present embodiments, has an outer diameter that is in a range of between 0.171 millimeters to 0.514 millimeters (0.0675 inches to 0.2025 inches), where the outer diameter is determined based on the type of material used to construct the sheath. In an alternative embodiment, the outer diameter of the sheath can be larger than 0.514 millimeters, where the final outer diameter of the sheath depends on the material used and the desired stiffness of the sheath. In one embodiment, the sheath is made of stainless steel. Alternatively, the sheath is made of a polymer, polymer blend and/or co-polymer, or a combination there of. For example, the sheath can be made of polyurethane or PEEK.

Figure 5:
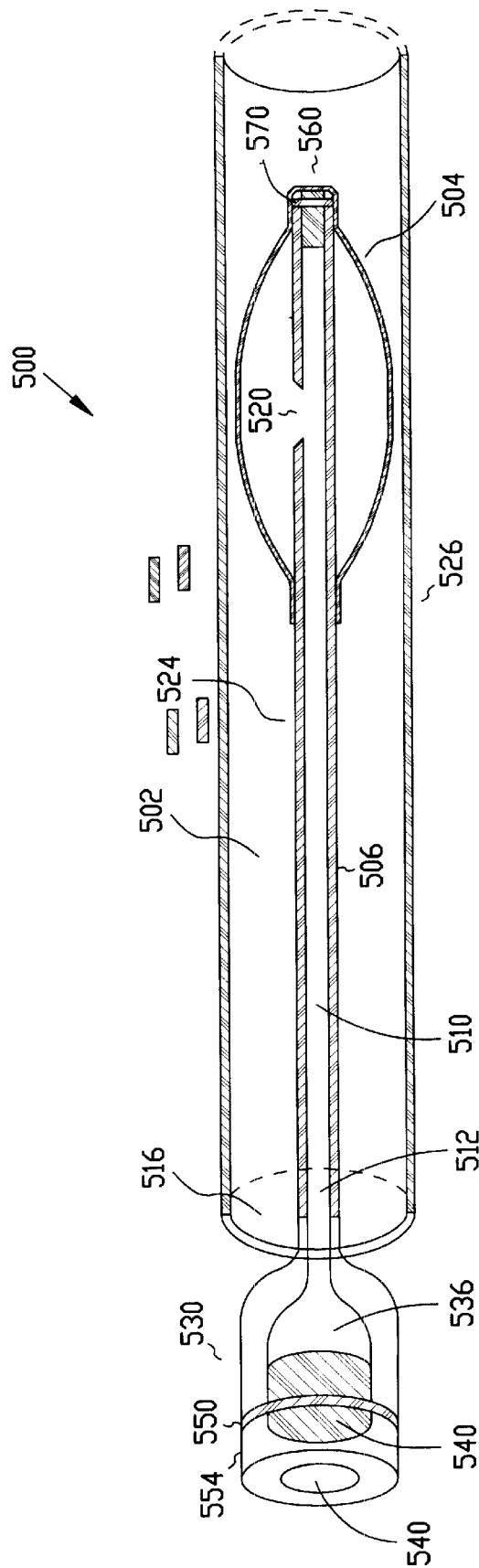
FIG. 5 is a schematic of an implantable device according to one embodiment of the present subject matter.

Referring now to FIG. 5 there is shown a schematic cross-sectional view of an implantable device assembly 500 according to one embodiment of the present subject matter. As previously described, the implantable device assembly 500 includes an implantable device 502 having an adjustable element 504 and a tubular elongate body 506, where the tubular elongate body 506 includes at least a first interior passageway 510 which extends longitudinally in the tubular elongate body 506 from a first opening 512 at the proximal end 516 to a second opening 520, and where the implantable device 502 is shown positioned within a channel 524 of a sheath 526. In one embodiment, the implantable device assembly 500 is similar to the implantable device assembly described from FIG. 2.

The implantable device assembly 500 further includes a rear port element 530, where the rear port element 530 is coupled to the proximal end 516 of the tubular elongate body 506. In one embodiment, the rear port element 530 is coupled to the proximal end 516 of the elongate body 506 using chemical adhesives, or alternatively, using sonic welding techniques as are known in the art. In an additional embodiment, the rear port element 530 and proximal end 516 are formed together in a polymer molding process, such as liquid injection molding, as are known in the art.

The rear port element 530 includes a cavity 536, where the cavity 536 is in fluid communication with the first opening 512 of the elongate body 506. In one embodiment, the rear port element 530 also includes an elastic septum 540 through which the cavity 536 is accessed, where the elastic septum 540 is a sealable after repeated pierces, for example, with a needle . In one embodiment, the elastic septum 540 is retained in the rear port element 530 by a clamp ring 550 located around the rear port element 530. In one embodiment, the clamp ring 550 is made of a biocompatible material, such as, for example, titanium. In one embodiment, the elastic septum 540 is made of a biocompatible material, such as, for example, silicone or polyurethane. The rear port element 530 has an outer diameter defined by outer surface 554 of the rear port element 530, where in one embodiment the rear port has an outer diameter of one (1) millimeter to ten (10) millimeters, (1) millimeter to six (6) millimeters, where four and one-half (4.5) millimeters is an possible diameter. The dimensions discussed for the rear port element apply to all embodiments of the present subject matter.

In one embodiment, the outer surface of the rear port element 530 and the adjustable element 504 are of a size (e.g., a diameter) that is smaller than an inner size (e.g., a diameter) of the channel 524 to allow the implantable device 502 to be moved longitudinally through the channel 524 of the sheath 526. In an alternative embodiment, the rear port element 530 is constructed of at least one material flexible enough to allow the size of the rear port element 530 in its relaxed state to be compressed to a size sufficiently small so that the implantable device 502 can be moved longitudinally through the channel 524 of the sheath 526. For the present embodiments, the tubular elongate body 506 has a stiffness sufficient to allow force applied at the proximal end of the tubular elongate body to move the implantable device at least partially through the channel of the sheath. In one embodiment, the stiffness of the tubular elongate body is determined based on the type of material used in constructing the tubular elongate body. Alternatively, support elements can be added to the tubular elongate body. For example, a metal coil can be placed longitudinally within the tubular elongate body to increase the stiffness of the tubular elongate body.

Once the implantable device 502 is positioned within a body, the adjustable element 504 is inflated by releasably connecting a flowable material source to the rear port element 530. In one embodiment, the flowable material source includes a syringe with a non-coring needle, where the needle is inserted through the elastic septum 540. A measured supply of fluid volume can be introduced into the implantable device, where the adjustable element 504 expands or contracts due to a volume of flowable material introduced into the cavity 536 of the rear port element 530 from the flowable material source. The adjustable element 504 is then used to at least partially and adjustably restrict the body lumen. Fluids suitable for infusing into the prothesis include, but are not limited to, sterile saline solutions, polymer gels such as silicone gels or hydrogels of polyvinylpyrrolidone, polyethylene glycol, or carboxy methyl cellulose for example, high viscosity liquids such as hyaluronic acid, dextran, polyacrylic acid, polyvinyl alcohol, or a radio-opaque fluid for example. Once the adjustable element 504 has been inflated, the needle is withdrawn from the septum of the rear port 530.

In an additional embodiment, a detectable marker 570 is imbedded in the continuous wall of the adjustable element 504. The detectable marker 570 allows the adjustable element 504 to be located and its shape to be visualized within the tissues of a patient using any number of visualization techniques which employ electromagnetic energy as a means of locating objects within the body. In one embodiment, the detectable marker 570 is constructed of tantalum and the visualization techniques used to visualize the adjustable element 504 are x-ray or fluoroscopy as are known in the art.

In an additional embodiment, a detectable marker is imbedded in the implantable device 502. For example, the detectable marker 570 is located at the distal end 560, (e.g., the tip) of the tubular elongate body 506. Alternatively, the detectable marker could be located in the continuous wall of the adjustable element 504. The detectable marker 570 allows the distal end 560, or the adjustable element 504, to be located and its shape to be visualized within the tissues of a patient using any number of visualization techniques which employ electromagnetic energy as a means of locating objects within the body. In one embodiment, the detectable marker 570 is constructed of tantalum and the visualization techniques used to visualize the distal end 560, or the adjustable element 504, are x-ray or fluoroscopy as are known in the art. In an additional embodiment, the sheath could also have a detectable marker, where the marker could be incorporated into, or on, the wall of the sheath. Alternatively, the entire sheath could be constructed so as to be radio-opaque.

Referring now to FIG. 6A, there is shown a schematic cross-sectional view of an implantable device assembly 600 according to one embodiment of the present subject matter. As previously described, the implantable device assembly 600 includes an implantable device 602 having an adjustable element 604, a tubular elongate body 606, and a detectable marker 605 imbedded at the distal end of the tubular elongate body 606 where the tubular elongate body 606 includes at least a first interior passageway 610 which extends longitudinally in the tubular elongate body 606 from a first opening 612 at the proximal end 616 to a second opening 620, and where the implantable device 602 is shown positioned within a channel 624 of a sheath 626. In the present embodiment, the adjustable element 604 is shown with a lower profile as compared to the other embodiments of the adjustable elements. In one embodiment, this lower profile is due to the adjustable element 604 being preshaped. In one embodiment, when the adjustable element 604 has no fluid volume inside its chamber, the walls of the adjustable element 604 can be folded around the tubular elongate body to provide for the lower profile. One example of folding the adjustable element 604 is shown in FIG. 6B. Folding the adjustable element 604 around, or onto, the tubular elongate body can also be done with any of the embodiments shown in the Figures.

The implantable device assembly 600 further includes a rear port element 630, which is releasably coupled to the proximal end 616 of the tubular elongate body 606. In one embodiment, the rear port element 630 includes a rear port wall 632 having an inner surface 634 and an outer surface 638. In an additional embodiment, the rear port element 630 includes an elastic septum 636. The inner surface 634 of the rear port wall 632 defines a cavity 634 and a rear port lumen 640, where the rear port lumen 640 has a lumen outlet 644. The lumen outlet 644 can then be coupled to the first interior passageway 610 to provide fluid communication between the cavity 634 and the chamber 650 of the adjustable element 604.

In one embodiment, the outer surface 638 of the rear port wall 632 is adapted to be coupled to the inner surface 646 of the tubular elongate body 606. For example, the outer surface 638 of the rear port element 630 can include one or more barbs 660 which are adapted to engage or seat in the wall 662 of the tubular elongate body 606 when the rear port element 630 is inserted into the first interior passageway 610. Alternatively, the outer surface 638 of the rear port element 630 can include one or more bumps which encircle the outer surface 638, where the one or more bumps have a diameter that is generally larger than the remainder of the outer surface 638 of the rear port element 630. Once engaged, the outer surface 638 and the first interior passageway 610 create a fluid tight seal. In one embodiment, a clamp element is positioned around the tubular elongate body 606 to further secure the rear port element 630 to the tubular elongate body 606. In one embodiment, the clamp element is a suture which is tied around the outer surface of the tubular elongate body.

Alternatively, the outer surface 638 of the rear port element 630 can have a tapered conical shape which increases in diameter from a first point at or near the distal end of the lumen outlet 644 to a second point proximal to the first point along the outer surface 638. In one embodiment, the diameter of the outer surface 638 at the first point is less than the diameter of the first interior passageway 610 and the diameter of the outer surface 638 at the second point is greater than the diameter of the first interior passageway. The first point of the outer surface 638 is then inserted into the first interior passageway 610 at the first opening 612 and moved longitudinally into the first interior passageway 610 until the outer surface 638 of the rear port element 630 seats against inner surface of the first interior passageway 610. In one embodiment, the rear port element is advanced into the first interior passageway 610 to create a fluid tight seal between the outer surface 638 of the rear port element 630 and the first interior passageway 610.

Alternatively, the outer surface 638 of the rear port element 630 can have a diameter that is equal to or greater than the inner diameter of the first interior passageway 610. When the rear port element 630 is inserted into the first interior passageway 610, the outer surface 638 of the rear port element 630 engages and seats against the inner surface of the first interior passageway 610. In one embodiment, a suture is tied around the tubular elongate body 606 to further secure the rear port element 630 to the tubular elongate body 606. Alternatively, the inner surface of the rear port element 630 can have a diameter that is equal to or greater than the outer diameter of the tubular elongate body 606. The inner surface of the rear port element 630 is then positioned around the outer surface of the tubular elongate body 606 to form a fluid tight seal.

In one embodiment, the tubular elongate body is constructed of at least one polymer, where the polymer can include thermoplastics and/or thermoset polymers. Examples of polymers suitable for constructing the tubular elongate body include silicone, silicone elastomers, polyurethane, polyethylene, PEEK and/or PET. In one embodiment, the tubular elongate body is created from an extruded length of polymer having any number of cross-section shown in the present Figures. Alternatively, the tubular elongate body is formed by casting a polymer in a mold which defines the surfaces, or boundaries, of the tubular elongate body.

Additionally, the tubular elongate body has a length between the proximal end and the distal end in a range of between two (2) centimeters to fifty (50) centimeters, where, in one embodiment, the length is determined by the size of the person and the position within the body that the implantable device is situated. In one embodiment, the length of the tubular elongate body can be adjusted to an appropriate length once the implantable device has been positioned within the body. The rear port element is then coupled to the elongate body and positioned subcutaneously.

One reason for having a releasably attachable rear port is to reduce the overall size (e.g., diameter) of the sheath used to introduce the implantable device. Typically, the rear port element has a size (e.g., one or more dimensions, such as an outer diameter) that is larger than the inner diameter of the sheath. Besides other potential problems, one difficulty is either extending the sheath around the rear port element, or providing a rear port element that can be compressed to a size which allows the implantable device to be moved through the sheath. In one embodiment, this problem is solved by utilizing the implantable device shown in any one of FIG. 1, FIG. 2, FIG. 3, FIG. 4 and FIG. 6, where the implantable device, absent the rear port element, is first slid through the sheath (FIGS. 1, 2, 3 and 6), or delivered through the use of the sleeve 424 (FIG. 4), the sheath removed from around the implantable device and the rear port element coupled to the tubular elongate body as will be more fully described below.

In an alternative embodiment, an implantable device is provided where the device includes a rear port element, a tubular elongate body and an adjustable element. The distal end of the implantable device is then positioned within the channel of the sheath and is moved longitudinally within the sheath either through the use of a push rod introduced into a second interior lumen, through force applied to the distal end of the tubular elongate body or through a sleeve moving within the sheath. In one embodiment, once the implantable device has moved through the sheath to the point where the adjustable element is positioned within the body, the adjustable element is inflated, the sleeve (if present) is removed, and the sheath is then withdrawn from the body. In the embodiments where a rear port element is present, however, the sheath must be passed around the rear port element in order to remove the sheath from the body.

Figure 7A:
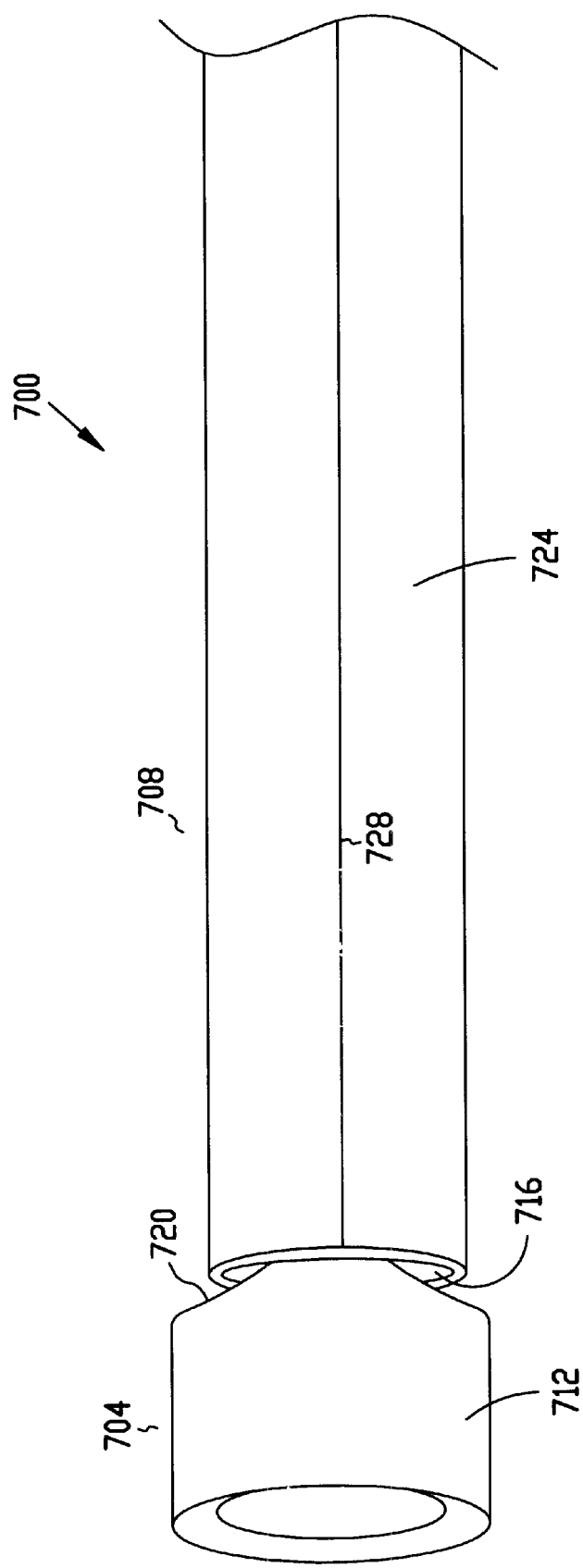
FIG. 7A is a schematic view of a sheath according to one embodiment of the present subject matter.

Referring now to FIG. 7A, there is shown one embodiment of an implantable device assembly 700. The implantable device assembly 700 includes an implantable device 704 and a sheath 708. The implantable device 704 is shown with a rear port element 712 positioned adjacent a channel opening 716 of the sheath 708. The sheath 708 further includes a wall 720, where the wall 720 has at least a first portion 724 and a second portion 728. In FIG. 7A, the second portion is shown as a first area of the wall that extends longitudinally along the body of the sheath 708, and a second area composes the remainder of the wall. In one embodiment, the second portion 728 of the wall is of a lesser strength as compared to the first portion 724 of the wall. This allows the sheath 708 to be separated along the second portion 728. In one embodiment, the sheath 708 is separated along the second portion 728 by force applied to the sheath 708 on either side of the second portion 728.

Figure 7B:
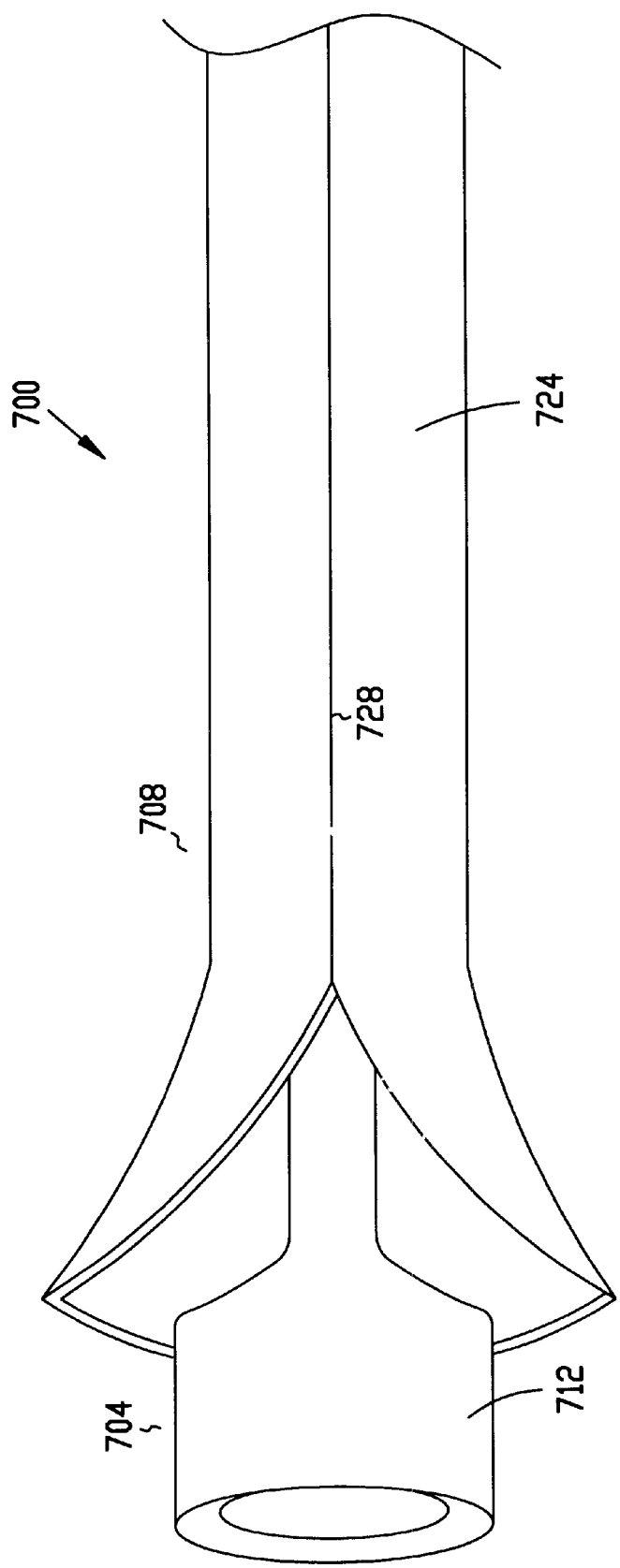
FIG. 7B is a schematic view of a sheath according to one embodiment of the present subject matter.

Referring now to FIG. 7B there is shown an embodiment of the implantable device assembly 700 where the sheath 708 is being separated along the second portion 728. As FIG. 7B shows, as the sheath 708 is separated along the second portion 728 the sheath 708 is opened into a more planar configuration. This planar configuration allows the sheath 708 to be passed around the rear port element 712. Thus, the dimension of the rear port element no longer effects whether the implantable device 704 can be removed from the sheath 708.

Figure 7C:
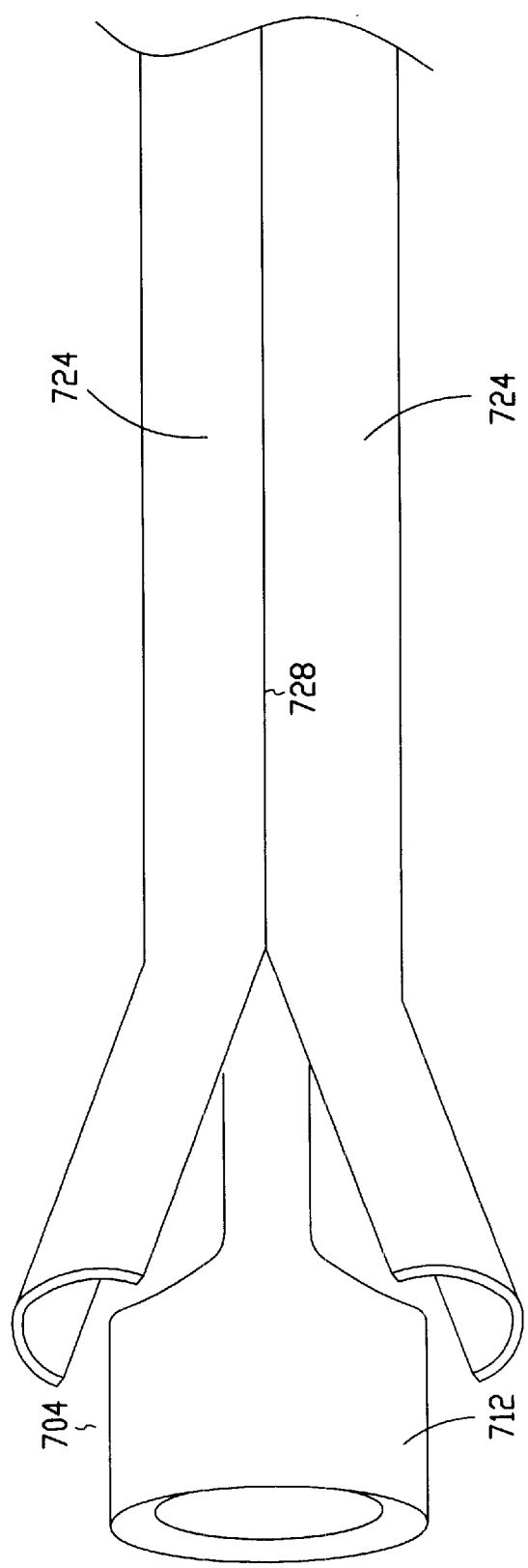
FIG. 7C is a schematic view of a sheath according to one embodiment of the present subject matter.

The sheath 708 shown in FIG. 7A and FIG. 7B is shown having one second portion 728. A sheath having additional second portions is also possible. For example, the sheath 708 in FIG. 7C is shown having two second portions 728, where the each of the two second portions 728 are positioned on opposite sides of the sheath 708.

Figure 8A:
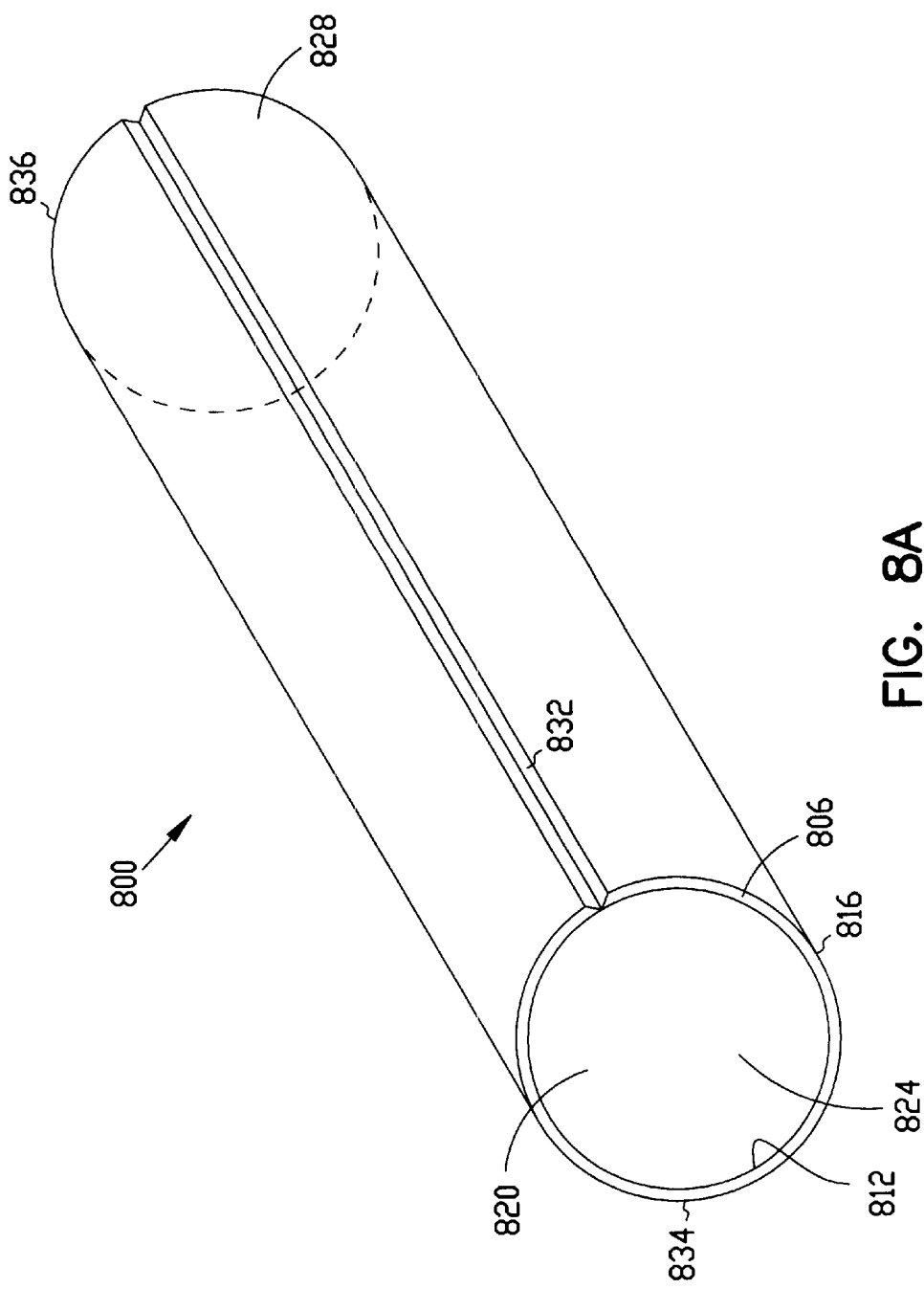
FIG. 8A is a schematic view of a sheath according to one embodiment of the present subject matter.

Referring now to FIG. 8A there is shown one embodiment of a sheath 800 according to the present subject matter. The sheath 800 includes a wall 806 having an inner surface 812 and an outer surface 816. In one embodiment, the inner surface 812 defines a channel 820 which passes through the sheath 800 from a first sheath opening 824 to a second sheath opening 828 (shown with hidden lines). The channel 820 of the sheath 800 has a size which is appropriate to receive at least a portion of an implantable device, and through which at least a portion of the implantable device can pass.

Sheath 800 also includes scorings, or a line of weakness, which extend longitudinally along the wall 806 from a proximal end 834 to a distal end 836. In one embodiment, a first scoring 832 is provided which extends longitudinally along the wall 806. In one embodiment, the first scoring 832 provides the second portion of the wall that is of the lesser strength as compared to the first portion. In the present embodiment, the second portion of the wall 806 is of lesser strength due to the absence of, or the thinning, of the material comprising the wall 806. In an alternative embodiment, the line of weakness is created by a plurality of closely spaced perforations, where the perforations extend through the wall 806. In one embodiment, the closely spaced perforations extend longitudinally along the sheath to create the line of weakness.

In one embodiment, scoring of the wall 806 can be accomplished during the process of creating the sheath. For example, the sheath can be created by extruding a polymer (or one or more polymers, including co-polymers) through a die which includes one or more protrusions for creating the scoring. Alternatively, the scoring could be accomplished after the sheath has been either extruded or cast, where the scorings are added by either removing or deforming the sheath material to create the region of lesser strength as compared to the remainder of the wall. Because of the lesser strength along the first portion, the sheath 800 can be split along the first scoring 832 when sufficient force is applied to the region of the first scoring 832 to cause the wall to separate. In addition, a stress concentration point in the form of a notch or nick at a proximal edge of the scoring can be used to ensure the sheath splits along the line, or path, of weakness.

Figure 8B:
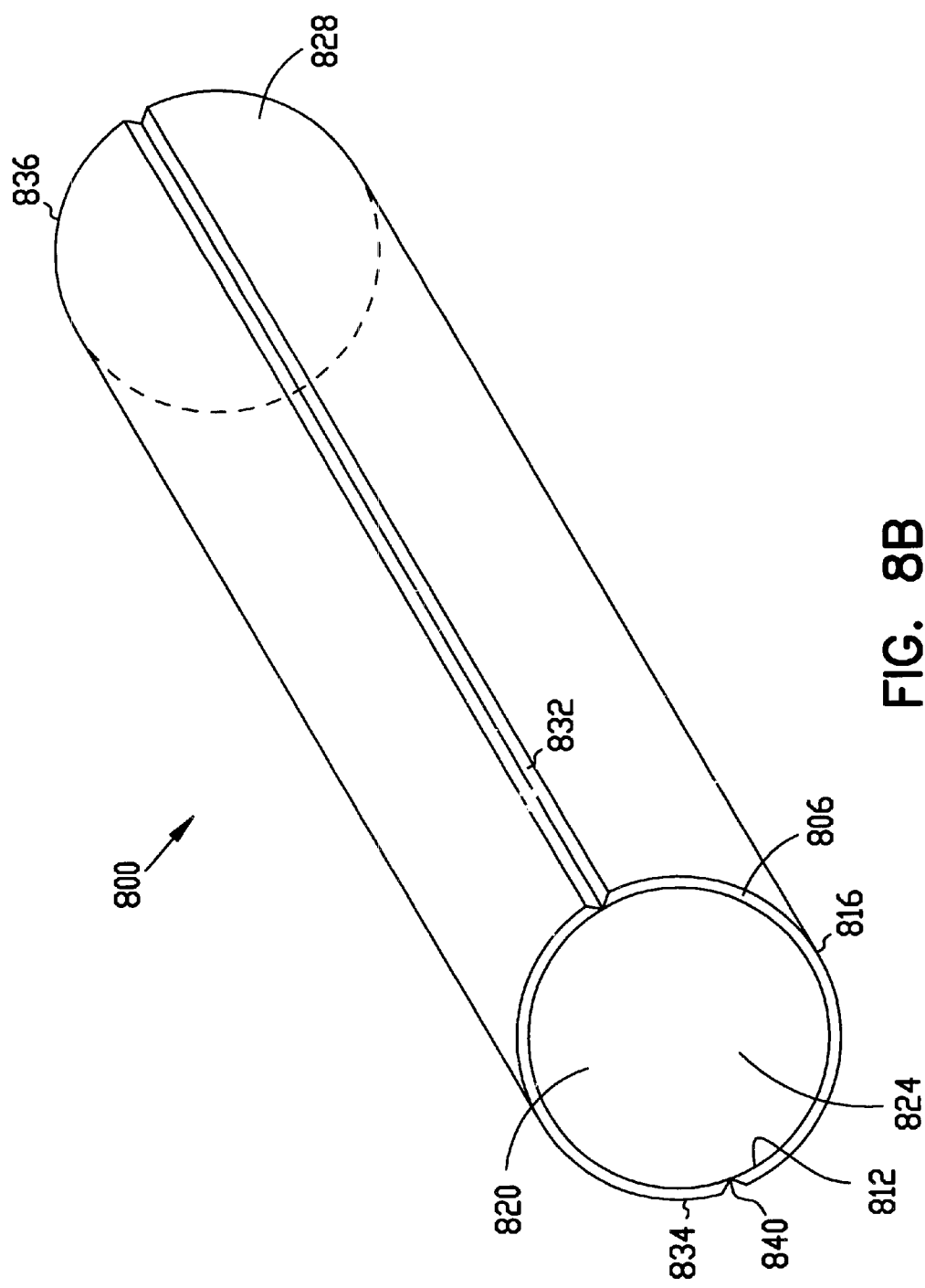
FIG. 8B is a schematic view of a sheath according to one embodiment of the present subject matter.

Referring now to FIG. 8B, there is shown an additional embodiment of the sheath 800 according to the present subject matter. The embodiment of the sheath 800 in FIG. 8B is shown where the wall 806 includes two scorings extending longitudinally along the wall 806 from a proximal end 834 to a distal end 836 to allow for the sheath 800 to be separated into two pieces. In FIG. 8B, the two scorings include the first scoring 832 and a second scoring 840. In one embodiment, the first and second scorings 832 and 840 are positioned on opposite sides of the sheath 800. Alternatively, the first and second scorings 832 and 840 can be located at any position on the wall 806.

Figure 9:
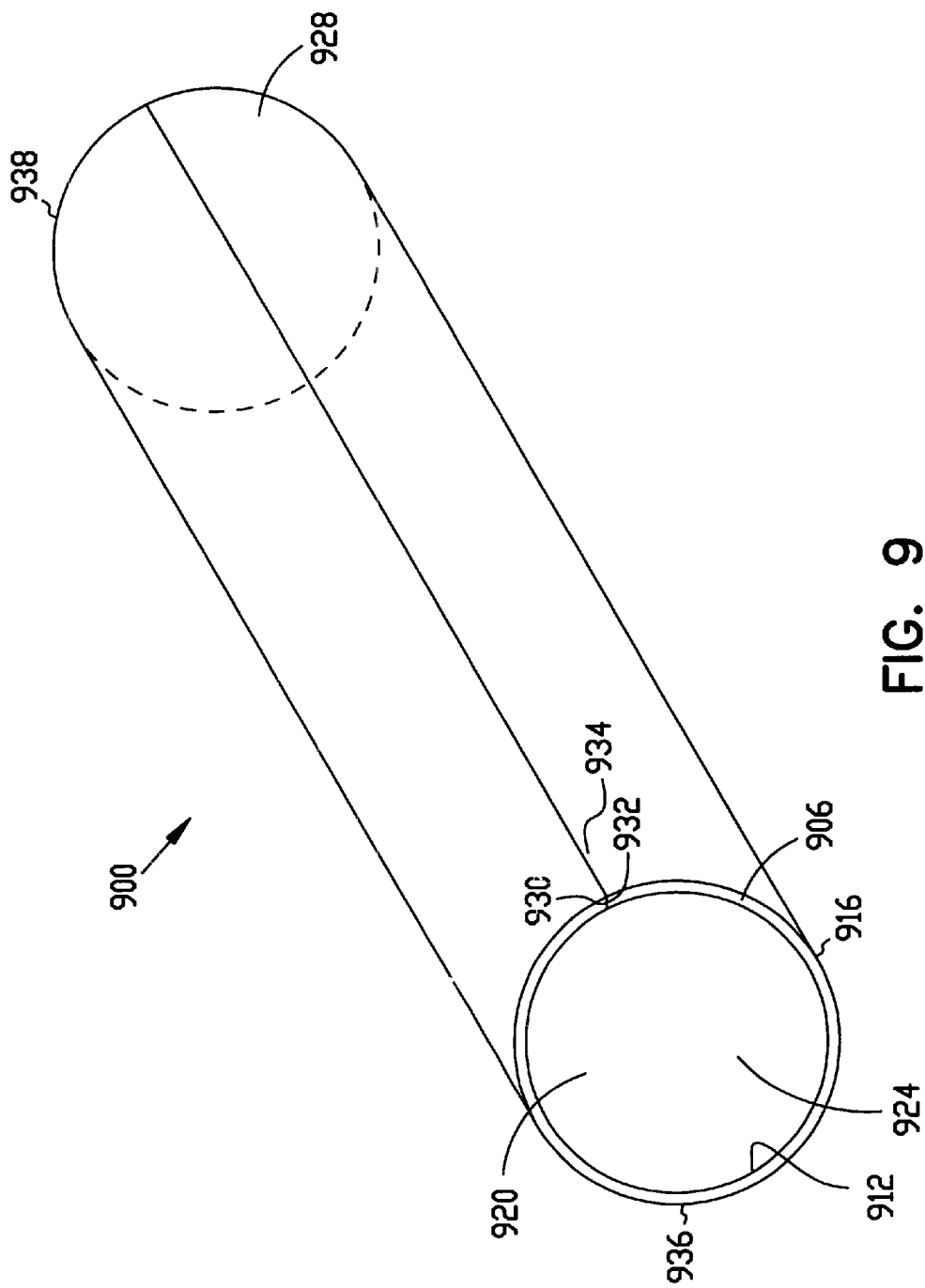
FIG. 9 is a schematic view of a sheath according to one embodiment of the present subject matter.

Referring now to FIG. 9, there is shown an alternative embodiment of a sheath 900 according to the present subject matter. The sheath 900 includes a wall 906 having an inner surface 912 and an outer surface 916. In one embodiment, the inner surface 912 defines a channel 920 which passes through the sheath 900 from a first sheath opening 924 to a second sheath opening 928 (shown with hidden lines). The channel 920 of the sheath 900 has a size which is appropriate to receive at least a portion of an implantable device, and through which at least a portion of the implantable device can pass.

Sheath 900 also includes a first edge 930 and a second edge 932, where the first edge 930 and the second edge 932 are closely adjacent and define a slit 934 between the edges. The slit 934 passes through the wall 906 and extends longitudinally along the wall 906 from a proximal end 936 to a distal end 938. In one embodiment, the slit 934 provides the second portion of the wall 906 that is of the lesser strength as compared to the first portion. In the present embodiment, the second portion of the wall 906 is of lesser strength due to the cut made through the wall 906. In one embodiment, creating the slit in the wall 906 can be accomplished during the process of creating the sheath. For example, the sheath can be created by extruding a polymer (or one or more polymers, including co-polymers) through a mold which has a protrusion for creating the slit. Alternatively, the slit could be accomplished after the sheath has been either extruded or cast, where the slit is added by cutting through the wall 906 along a path the extends longitudinally along the sheath 900. The presence of the slit 934 allows the sheath to be separated at the slit 934 so that the sheath can be passed around the implantable device (not shown). In one embodiment, the sheath is constructed of a elastic material which is adapted to flex so as to allow the implantable device to pass through the slit in the sheath.

Figure 10:
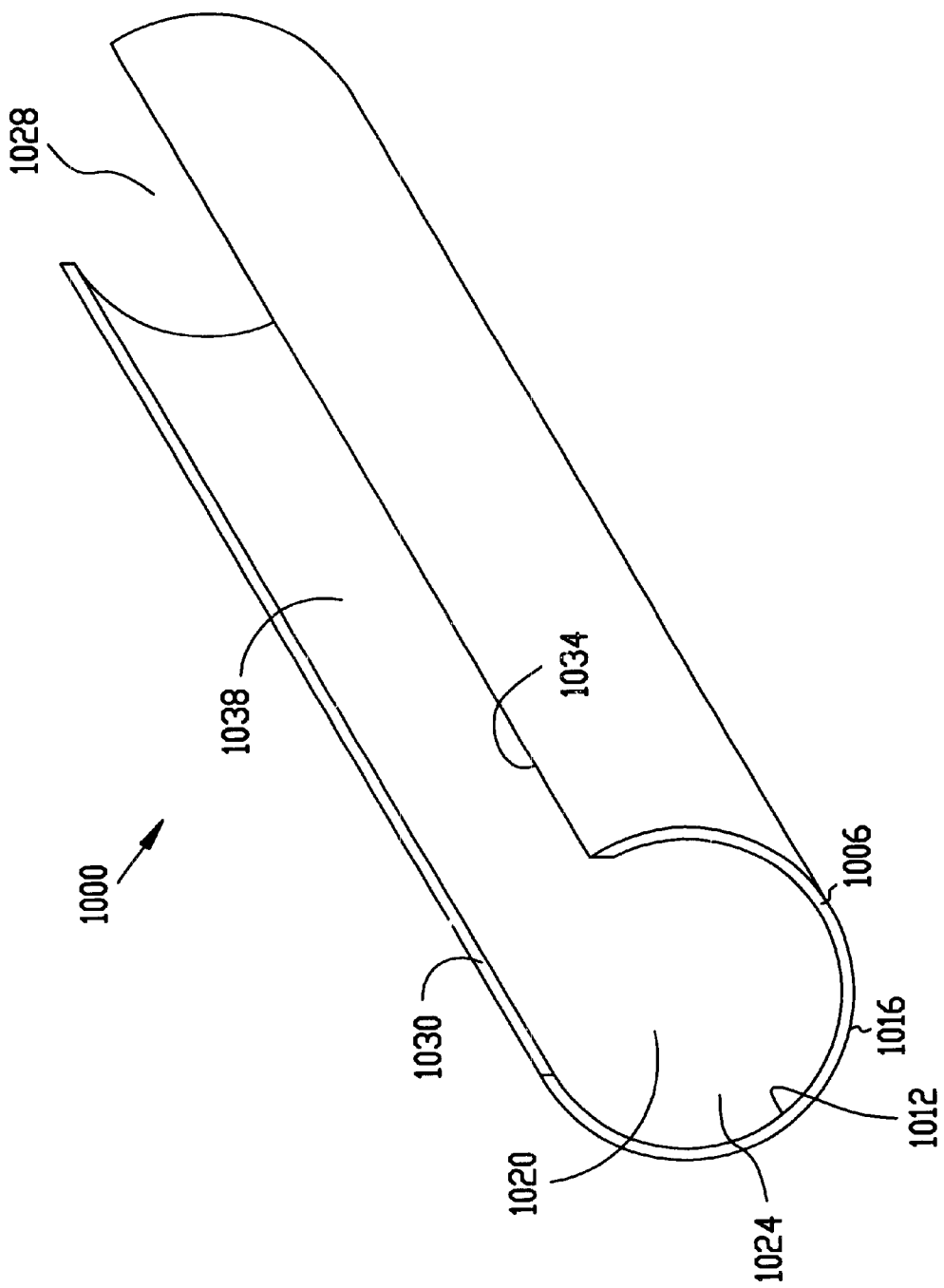
FIG. 10 is a schematic view of a sheath according to one embodiment of the present subject matter.

Referring now to FIG. 10, there is shown an additional embodiment of a sheath 1000 according to the present subject matter. The sheath 1000 includes a wall 1006 having an inner surface 1012 and an outer surface 1016. In one embodiment, the inner surface 1012 defines a channel 1020 which passes through the sheath 1000 from a first sheath opening 1024 to a second sheath opening 1028 opposite the first sheath opening 1024. The channel 1020 of the sheath 1000 has a size and a volume which is appropriate to receive at least a portion of an implantable device, and through which at least a portion of the implantable device can pass.

Sheath 1000 also includes a first edge 1030 and a second edge 1034 that are spaced to define a slot 1038 in the wall 1006. In one embodiment, the distance between the first edge 1030 and the second edge 1034 is equal to or greater than the outer diameter of the tubular elongate body. Alternatively, the distance between the first edge 1030 and the second edge 1034 is less than the outer diameter of the tubular elongate body, where the tubular elongate body is constructed of an elastic polymer which deforms to allow the tubular elongate body to pass through the slot 1038.

Alternatively, the slot is sufficiently large to afford the passage of at least one of the rear port, tubular elongate body and/or the adjustable element of an implantable device through the slot 1038, where any of the portions of the implantable device are deformable to allow them to pass through the slot. In one embodiment, the wall 1006 has sufficient stiffness to maintain its shape when inserted into a body (as will be described below) and when an implantable device is passed into the channel, but yet has sufficient elasticity to allow the wall 1006 to deform as the implantable device is passed through the slot 1038.

Figure 11:
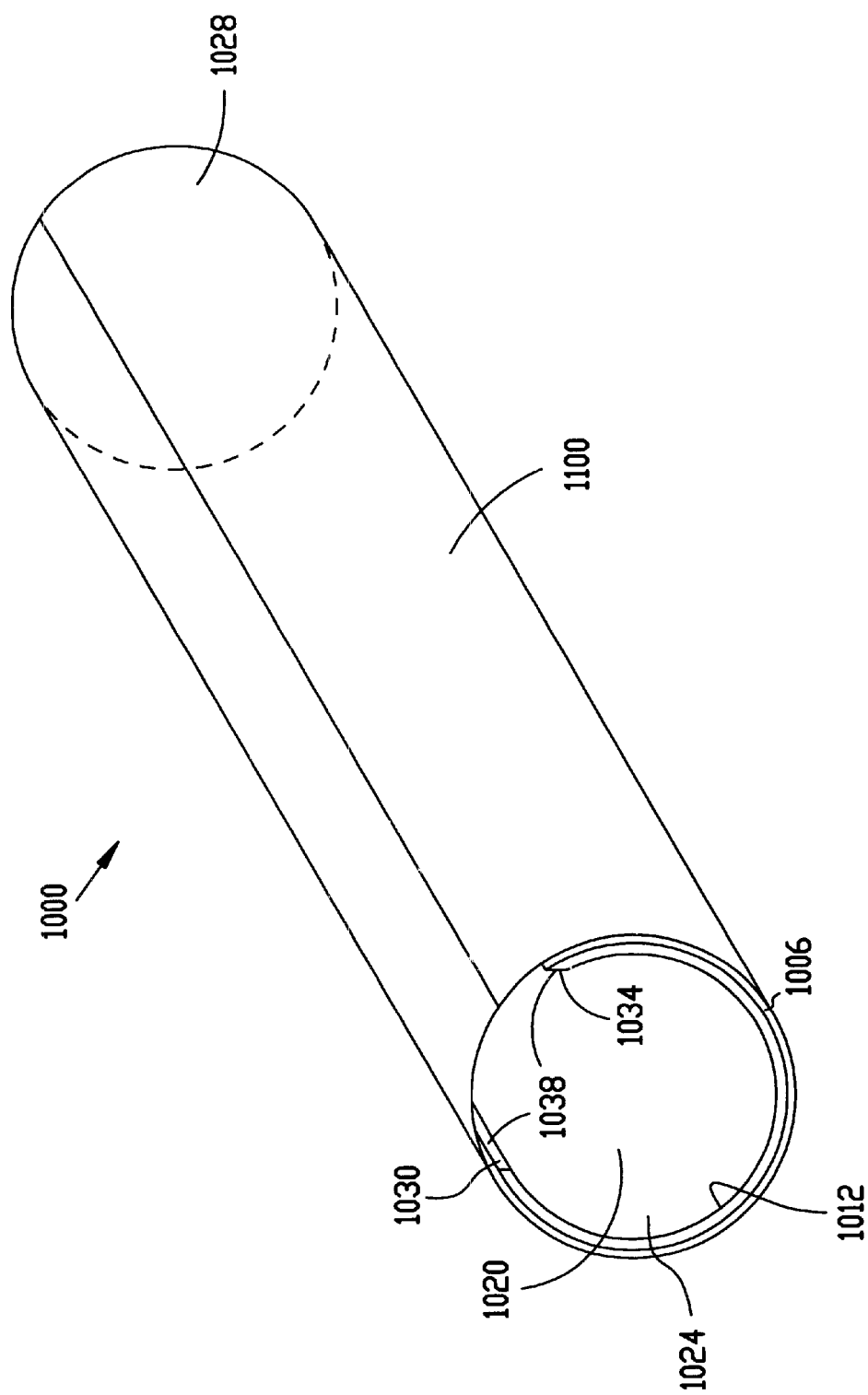
FIG. 11 is a schematic view of a sheath according to one embodiment of the present subject matter.

Referring now to FIG. 11, there is shown an additional embodiment of the sheath 1000 according to the present subject matter. The sheath 1000 further includes a layer 1100 over the outer surface 1016. In one embodiment, the layer 1100 traverses, or extends over, the slot 1038 to form a continuous channel 1020 through the sheath 1000. In one embodiment, the layer 1100 is made of a material which has a lesser strength than the wall 1006 of the sheath 1000. In one embodiment, the layer 1100 is adapted to develop a tear and to rip at least longitudinally along the major axis of the sheath as the implanted device is passed through the slot 1038 during insertion. Alternatively, the layer 1100 includes a slit 1110 which passes through the layer 1100, where the slit 1110 is adapted to allow the implanted device to pass through the slot and the slit during insertion.

In one embodiment, the layer is formed by dipping, or casting the sheath 1000 in a polymer in a softened state (either through heat for a thermoplastic or pre-cross linked state for a thermosetting polymer), where the sheath 1000 is provided with a removable casting core which fills the volume of the channel 1020 and allows the layer to be formed over the slot 1038. In one embodiment, the layer 1100 is formed from polyurethane, Teflon, nylon, nylon elastomers, Pebax™, Polyethylene, silicone, or other flexible polymers or polymer blends as are known.

Figure 12A:
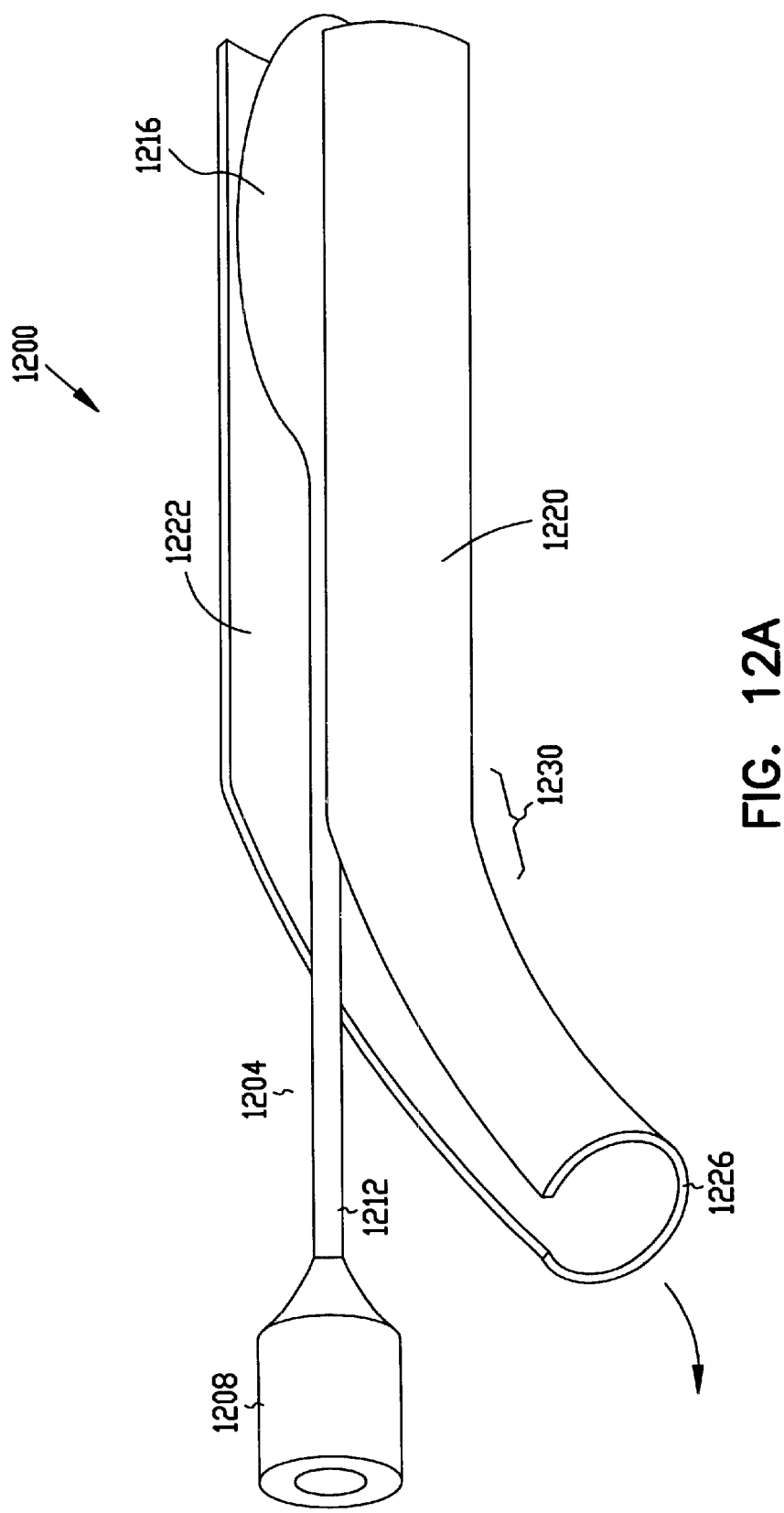
FIG. 12A is a schematic cross-sectional view of the implantable device assembly according to one embodiment of the present subject matter.

FIG. 12A shows one embodiment of an implantable device assembly 1200 according to the present subject matter. The implantable device assembly 1200 includes an implantable device 1204, having a rear port element 1208, a tubular elongate body 1212 and an adjustable element 1216. The implantable device assembly 1200 also includes a sheath 1220, where in the present embodiment the sheath 1220 includes a slot 1222 as previously described.

In one embodiment, as the sheath 1220 is removed from around the implantable device 1204, the wall 1226 of the sheath is bent or deformed, shown generally at 1230, to allow the components of the implantable device 1204 to pass through the slot 1222. As the sheath 1220 is being bent to allow the implantable device 1204 to pass through the slot 1222 the sheath can also be pulled in the general direction of the rear port 1208, which will be more fully understood later in this document to be important in removing the sheath 1220 from a location in a body where an implantable device is desired.

Figure 12B:
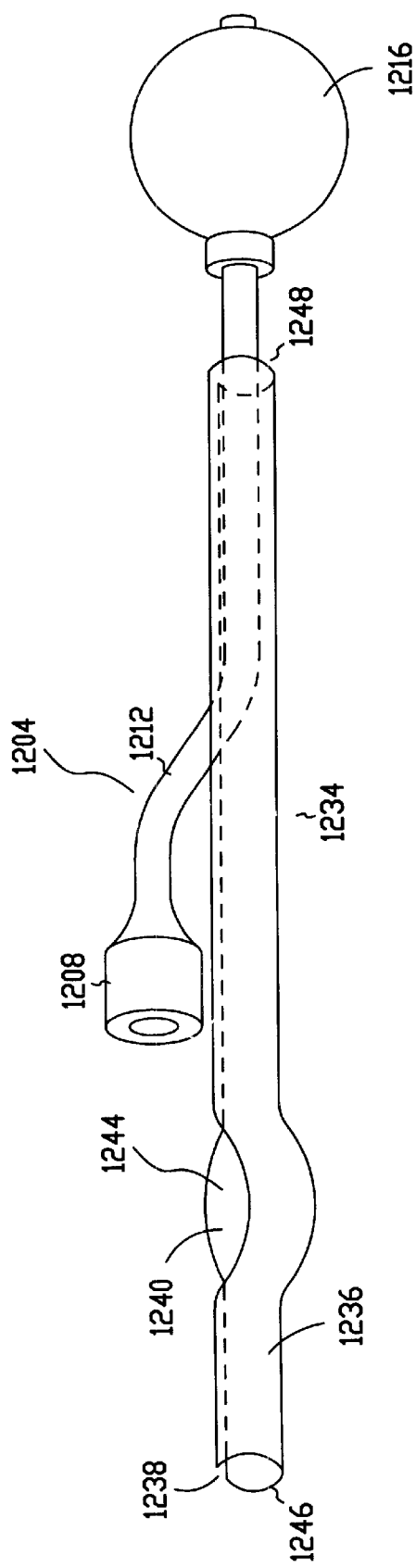
FIG. 12B is a schematic cross-sectional view of the implantable device assembly according to one embodiment of the present subject matter.

FIG. 12B shows an additional embodiment of an implantable device assembly 1234 according to the present subject matter. The implantable device assembly 1234 includes an implantable device 1204, having a rear port element 1208, a tubular elongate body 1212 and an adjustable element 1216. The implantable device assembly 1234 also includes a sleeve 1236, where in the present embodiment the sleeve 1236 includes a slot 1238 and an inner surface 1240. In one embodiment, the inner surface 1240 defines a receptacle region 1244 which has a shape and a size to receive at least a portion of the rear port element 1208.

In the present embodiment, the implantable device 1204 is shown with the adjustable element 1216 in an expanded state. In one embodiment, the implantable device 1204 is moved at least partially through a sheath (not shown) through force applied at the proximal end 1246 of the sleeve 1236. As previously described, the distal end 1248 of the sleeve 1236 abuts the ridge, or ledge, formed at the point where the tubular elongate body 1212 is connected to and sealed to the adjustable element 1216. Once the implantable device 1204 has been positioned in the body, fluid is injected into the rear port element 1208 to inflate the adjustable element 1216. Once the adjustable element 1216 is inflated, the sheath is removed (as previously described). The sleeve 1236 is then removed from around the implantable device 1204 by first removing the rear port element 1208 from the receptacle region 1244 and then passing the tubular elongate body 1212 through the slot 1238 of the sleeve 1236. In the present embodiment, the sleeve 1236 is sufficiently stiff so that the walls of the sleeve 1236 flex very little, if at all, as the tubular elongate body 1212 deforms to pass through the slot 1238.

Figure 13:
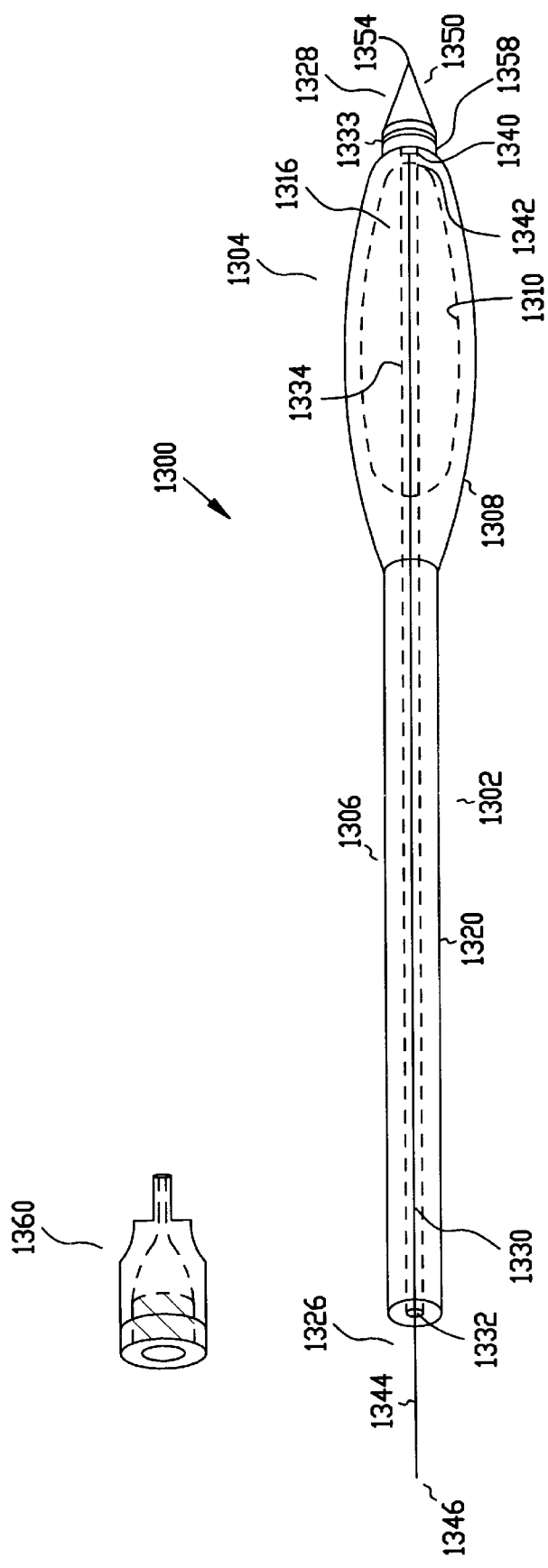
FIG. 13 is a schematic of an implantable device according to one embodiment of the present subject matter.

Referring now to FIG. 13, there is shown a schematic view of the implantable device assembly 1300 according to one embodiment of the present subject matter. The implantable device assembly 1300 is shown to include an implantable device 1302 which has an adjustable element 1304 and a tubular elongate body 1306. In one embodiment, the adjustable element 1304 includes a continuous wall 1308, including an inner surface 1310 defining a chamber 1316. The tubular elongate body 1306 includes a peripheral surface 1320, a proximal end 1326 and a distal end 1328. In one embodiment, the peripheral surface 1320 is connected to and sealed to the adjustable element 1304 as previously described.

The tubular elongate body 1320 also includes at least a first interior passageway 1330 which extends longitudinally in the tubular elongate body 1320 from a first opening 1332 at the proximal end 1326 to a second opening 1334. In one embodiment, the second opening 1334 is in fluid communication with the chamber 1316 of the implantable device 1302 for adjustably expanding or contracting the adjustable element 1304 by flowable material introduced through the first opening 1332. Additionally, a detectable marker 1333 is located at or on the distal end of the tubular elongate body 1320 to allow for the position of the implantable device 1300 be located within the tissues of a patient. Alternatively, the detectable marker is imbedded in the continuous wall of the adjustable element 1304.

In one embodiment, the first interior passageway 1330 includes a closed end 1340, where the closed end 1340 is positioned distal to both the first opening 1332 and second opening 1334. The closed end 1340 is of sufficient strength and hardness to receive a distal end 1342 of a push rod 1344, where the closed end 1340 transfers force applied at a proximal end 1346 of the push rod 1344 to the implantable device 1300. In one embodiment, the first interior passageway 1330 is of sufficient diameter to receive the push rod 1344 which contacts the closed end 1340 to allow force applied to the push rod 1344 to move the implanted device 1302.

The implantable device assembly 1300 further includes a tip 1350. In one embodiment, the distal end 1328 of the tubular body 1320 forms the tip 1350. In one embodiment, the tip 1350 is suitable to penetrate the tissue of a patient, where the tip 1350 includes at least a distal end 1354 which is sharped to afford the ability to insert the tip 1350 and the implantable device 1302 into the tissue of a patient. This configuration of the implantable device assembly 1300 allow for the implantable device 1302 to be delivered into the tissue of the patient without the need for a sheath. The tip also has a conical configuration to allow for the tissue being penetrated by the implantable device 1302 to pass over the tip 1350 and the body of the implantable device 1302. In an additional embodiment, the tip 1350 further includes one or more sharpened edges which extend from the distal end 1354 of the tip 1350 toward a proximal end 1358 of the tip 1350. In an additional embodiment, the adjustable element 1304 is adapted to expand under pressure from a volume of flowable material introduced through the first opening to at least partially envelop the tip 1350.

The present embodiment shows an example of a "self-dilating" device, where the implantable device is used to create its own pathway into the body of the patient. An advantage of the present embodiment is that the size of the opening created for inserting the implantable device is keep to a minimum, as only a channel the approximate size of the implantable device is created. Also, the surgical procedure is expedited as there are fewer items (e.g., obturator, sheath etc.) to insert prior to the actual delivery of the implantable device.

The tip 1350 used on the implantable device 1302 can be constructed of a variety of materials. In one embodiment, the tip 1350 is made of a hard plastic, such as polyurethane or PET. Alternatively, the tip 1350 is constructed of a biodegradable, or bioabsorbable, material, such as polyglycolic acid or polylactic acid, a dissolvable material such as a starch, or a material that is initially hard, but becomes soft after exposure to moisture, such as a hydrogel material. In this embodiment the tip is bonded to the distal end 1328 of the tubular elongate body. In one embodiment, the bonding is accomplished with a medical grade adhesive, such as silicone. Alternatively, the tip 1350 is cast onto the distal end 1328 of the tubular elongate body 1320, where the distal end 1328 has been configured and shaped to receive the tip material so as to lock the tip 1350 in place.

The implantable device assembly 1300 further includes a rear port element 1360, which is releasably coupled to the proximal end 1326 of the tubular elongate body 1320. The rear port element 1360 is similar to the rear port element previously described, and is adapted to be coupled to the tubular elongate body 1320 to create a fluid tight seal between the outer surface of the rear port element 1360 and the inner surface of the first interior passageway of the tubular elongate body 1320.

Figure 14:
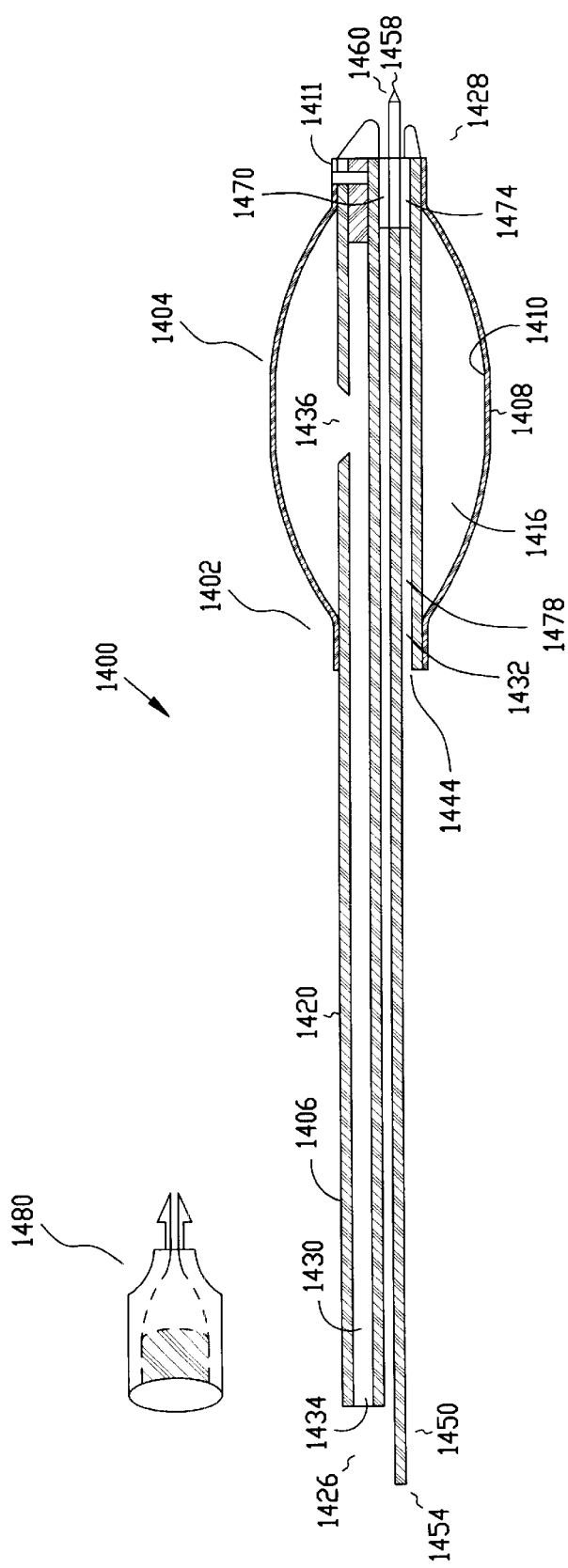
FIG. 14 is a schematic of an implantable device according to one embodiment of the present subject matter.

Referring now to FIG. 14, there is shown an additional embodiment of an implantable device assembly 1400 according to the present subject matter. The implantable device assembly 1400 is shown to include an implantable device 1402 which has an adjustable element 1404 and a tubular elongate body 1406. The tubular elongate body 1406 includes a peripheral surface 1420, a proximal end 1426 and a distal end 1428. In one embodiment, the peripheral surface 1420 is connected to and sealed to the adjustable element 1404 as previously described. In one embodiment, the adjustable element 1404 includes a continuous wall 1408, including an inner surface 1410 defining a chamber 1416 and at least one detectable marker 1411 positioned at the distal end 1428 of the tubular elongate body 1406. Alternatively, the maker 1411 can be embedded in the continuous wall of the adjustable element 1404 to allow for the position of the implantable device 1400 to be located and its shape to be visualized within the tissues of a patient. Detectable markers can also be embedded in the tubular elongate body 1406.

The tubular elongate body 1406 includes a first interior passageway 1430 and a second interior passageway 1432. In one embodiment, the first interior passageway 1430 extends longitudinally in the tubular elongate body 1406 from a first opening 1434 at the proximal end 1426 to a second opening 1436. The second opening 1436 is in fluid communication with the chamber 1416 of the implantable device for adjustably expanding or contracting the adjustable element 1404 by flowable material introduced through the first opening 1434, as previously described.

The second interior passageway 1432 extends longitudinally along at least a portion of the tubular elongate body 1406 from an inlet 1444 to an outlet 1446. In one embodiment, the second interior passageway 1432 is of sufficient diameter to receive a push rod 1450. The push rod 1450 has a proximal end 1454 and a distal end 1458, where the distal end 1458 of the push rod 1450 has a tip 1460 which is has a sharp point. In one embodiment, the sharp tip 1460 of the push rod 1450 extends through the outlet 1446 of the second interior passageway 1432 to provide the initial cutting tip of the implantable device apparatus 1400. In one embodiment, the distal end 1428 of the tubular elongate body 1420 has a conical taper which extends from the tip 1460 to allow the distal end 1428 to create a uniform conical shape suitable for penetrating tissue.

In one embodiment, to position the push rod 1450 within the second interior passageway 1432 with only the tip 1460 protruding from the distal end 1428, there is provided a first shoulder 1470 in the second interior passageway 1432 against which a corresponding second shoulder 1474 on the push rod 1450 seats. In one embodiment, the first shoulder 1470 is formed by a change in diameter of the second interior passageway 1432, where the inner surface 1478 of the second interior passageway 1432 changes from having a first passageway diameter to a second passageway diameter, where the second diameter is smaller than the first diameter. The second shoulder 1474 is also formed by a change in diameter of the push rod 1450, where the exterior surface of the push rod 1450 changes from having a first rod diameter to a second rod diameter. Once the push rod 1450 is inserted into the second channel it is advanced so that the second shoulder 1474 abuts the first shoulder 1470 and so that the tip 1460 protrudes from the distal end 1428. Force applied to the push rod 1450 can then be transferred to the implanted device 1402 so that it may be advanced into the tissue of a patient.

The implantable device assembly 1400 further includes a rear port element 1480, which is coupled to the proximal end 1426 of the tubular elongate body 1420. In one embodiment, the rear port element 1480 is similar to the rear port element previously described, and is adapted to be releasably coupled to the tubular elongate body 1420 to create a fluid tight seal between the outer surface of the rear port element 1480 and the inner surface of the first interior passageway of the tubular elongate body 1420.

Figure 15:
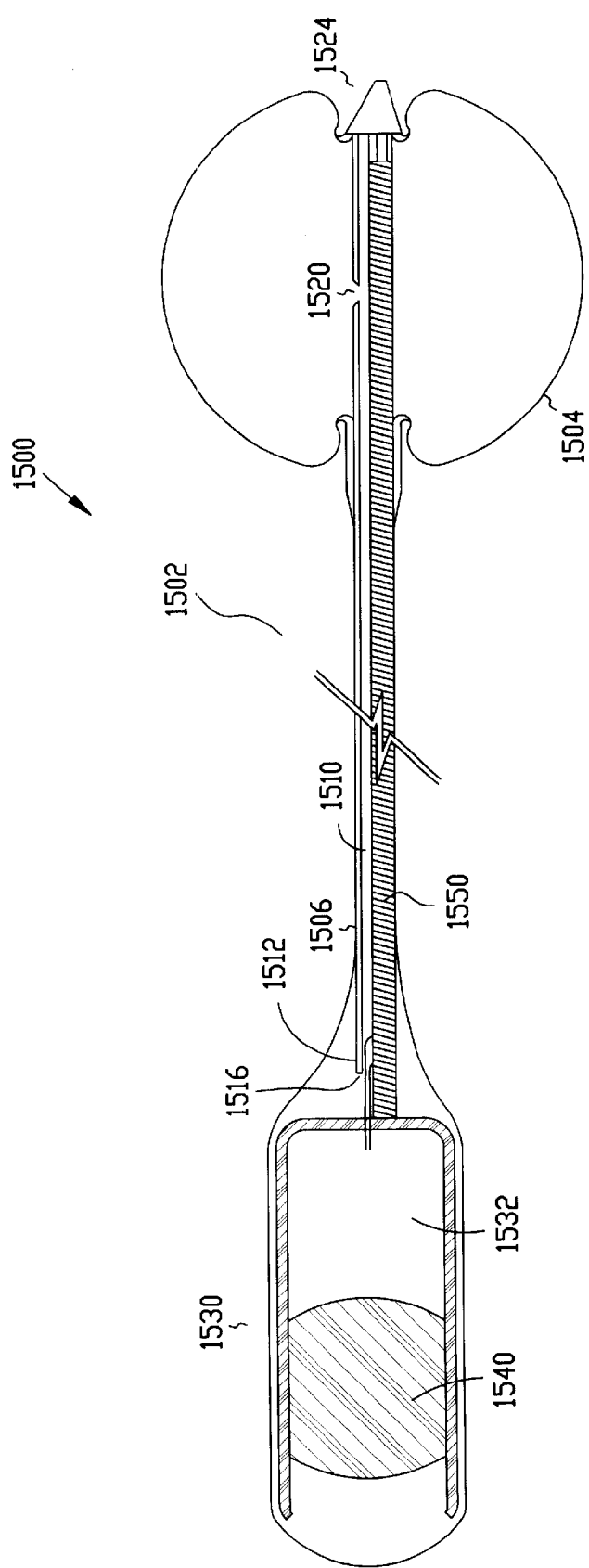
FIG. 15 is a schematic of an implantable device assembly according to one embodiment of the present subject matter.

Referring now to FIG. 15 there is shown a schematic cross-sectional view of an implantable device assembly 1500 according to one embodiment of the present subject matter. As previously described, the implantable device assembly 1500 includes an implantable device 1502 having an adjustable element 1504 and a tubular elongate body 1506, where the tubular elongate body 1506 includes at least a first interior passageway 1510 which extends longitudinally in the tubular elongate body 1506 from a first opening 1512 at the proximal end 1516 to a second opening 1520. The implantable device assembly 1500 also includes a tip 1524, where the tip 1524 has a end suitable for insertion of a tip and device into tissue of the patient as previously discussed.

The implantable device assembly 1500 further includes a rear port element 1530, where the rear port element 1530 is coupled to the proximal end 1516 of the tubular elongate body 1506. The rear port element 1530 includes a cavity 1532 in fluid communication with the first opening 1512 of the first interior passageway 1510. In one embodiment, the rear port element 1530 also includes an elastic septum 1540 through which the cavity 1532 is accessed. In one embodiment, the elastic septum 1540 has a structure, a size and function as previously described. As shown in FIG. 15, the elastic septum 1540 has a bulbous configuration.

In the present embodiment, the tubular elongate body 1506 has a stiffness sufficient to allow force applied at the proximal end of the tubular elongate body 1506 to move the implantable device 1502 through soft tissue of a patient. In one embodiment, the stiffness of the tubular elongate body is determined based on the type of material used in constructing the tubular elongate body. Alternatively, support elements can be added to the tubular elongate body. For example, a metal coil 1550 is placed longitudinally within the tubular elongate body to increase the stiffness of the tubular elongate body 1506. In one embodiment, the metal coil 1550 allows force applied along the longitudinal axis of the implantable device 1502 to be transferred to the tip 1524.

FIG. 15 also shows one embodiment of the adjustable element 1504 in an inflated state. In the present embodiment, the adjustable element 1504 is adapted to partially envelop the tip 1524. One reason for enveloping the tip with the adjustable element 1504 is to protect the tissue in the implant area from the tip 1524. The example in FIG. 15 is just one example of a tip being enveloped by the adjustable element, and other configurations of enveloping the tip can be imagined, such as the tip being completely surrounded by the adjustable element.

Figure 16A:
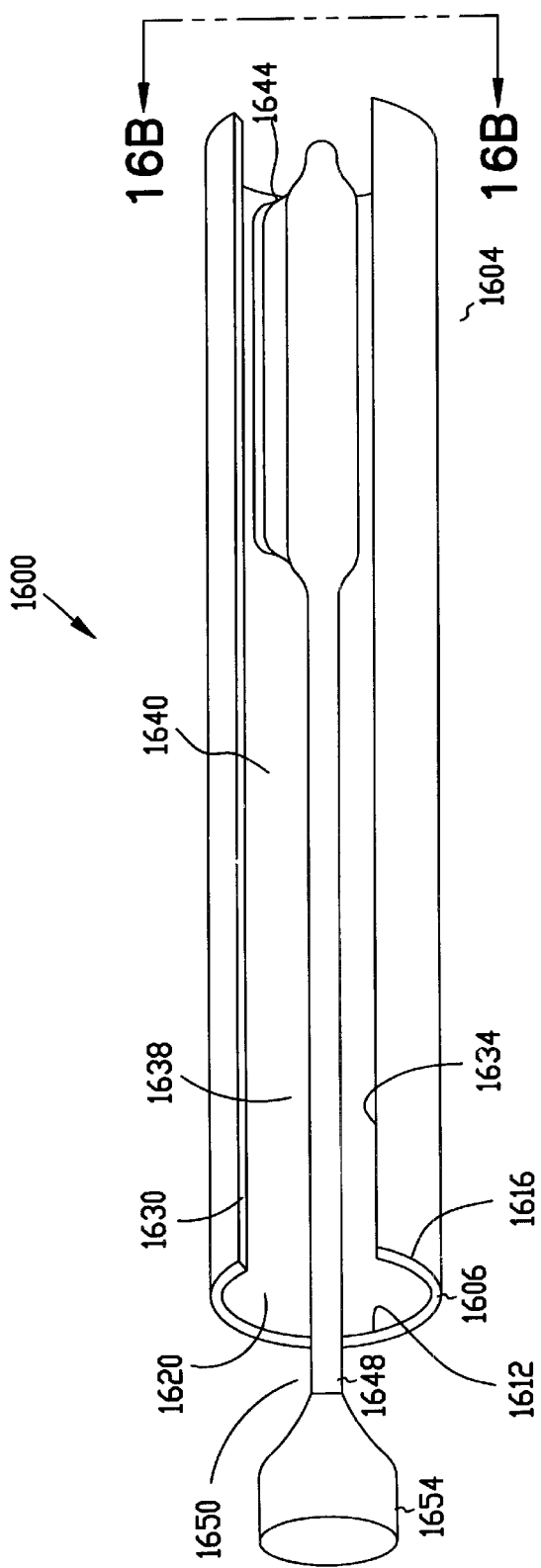
FIG. 16A is a schematic of an implantable device according to one embodiment of the present subject matter.

Referring now to FIG. 16A, there is shown an additional embodiment of a implantable medical device assembly 1600 according to the present invention. The implantable medical device assembly 1600 includes a sheath 1604 having a wall 1606 having an inner surface 1612 and an outer surface 1616. In one embodiment, the inner surface 1612 defines a channel 1620 which passes through the sheath 1604 from a first sheath opening 1624 to a second sheath opening 1628 opposite the first sheath opening 1624. The channel 1620 of the sheath 1604 has a size and a volume which is appropriate to receive at least a portion of an implantable device, and through which at least a portion of the implantable device can pass. Sheath 1604 also includes a first edge 1630 and a second edge 1634 that are spaced to define a slot 1638 in the wall 1606. In one embodiment, the distance between the first edge 1630 and the second edge 1634 is equal to or greater than the outer diameter of the tubular elongate body.

The implantable medical device assembly 1600 further includes an implantable medical device 1640. As previously described, the implantable device 1640 includes an adjustable element 1644 and a tubular elongate body 1648, where the tubular elongate body 1648 includes at least a first interior passageway which extends longitudinally in the tubular elongate body 1648 from a first opening at the proximal end 1650 to a second opening, and where the implantable device 1640 is shown positioned within the channel 1620 of the sheath 1604.

The implantable device assembly 1640 further includes a rear port element 1654, as previously described, where the rear port element 1654 is coupled to the proximal end 1650 of the tubular elongate body 1648. In one embodiment, the rear port element 1654 is coupled to the proximal end 1650 of the elongate body 1648 using chemical adhesives, or alternatively, using sonic welding techniques as are known in the art. In an additional embodiment, the rear port element 1654 and proximal end 1650 are formed together in a polymer molding process, such as liquid injection molding, as are known in the art.

Figure 16B:
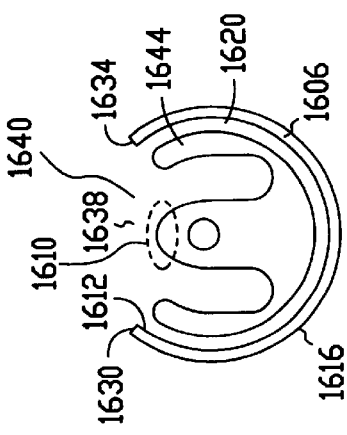
FIG. 16B is a schematic of an implantable device according to one embodiment of the present subject matter.
Figure 16C:
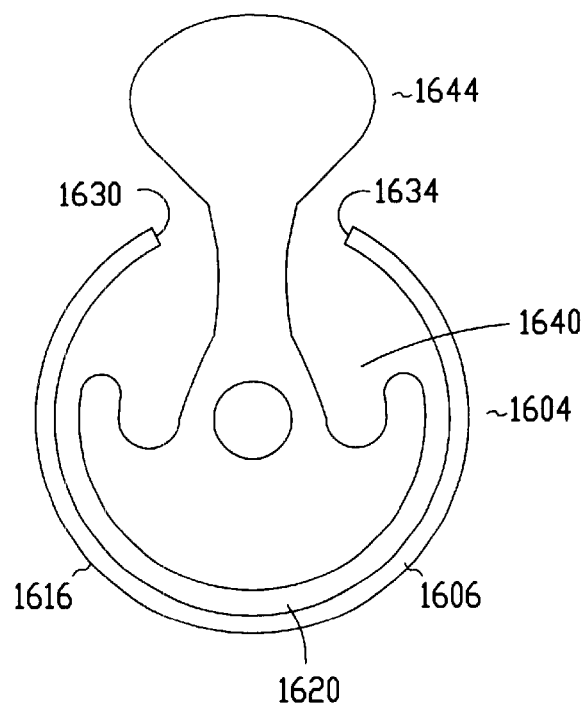
FIG. 16C is a schematic of an implantable device according to one embodiment of the present subject matter.
Figure 16D:
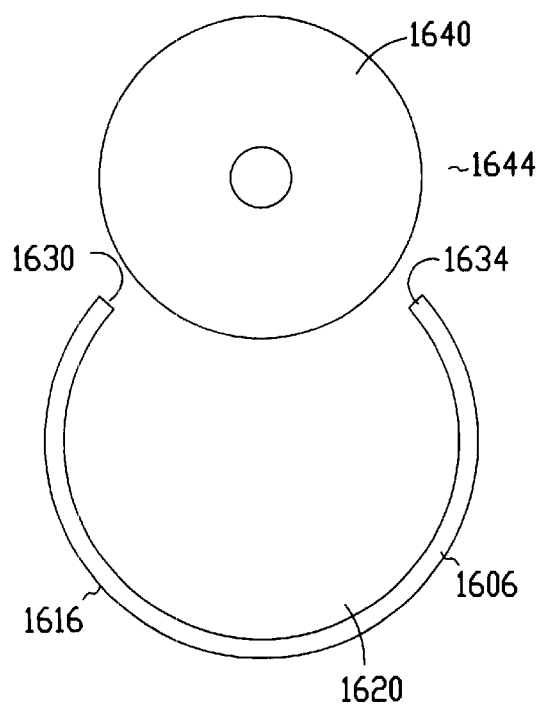
FIG. 16D is a schematic of an implantable device according to one embodiment of the present subject matter.

In the present embodiment, the adjustable element 1644 is shown folded into the channel 1620 of the sheath 1604. In one embodiment, the folding of the adjustable element 1644 is shown in FIG. 16B, where the adjustable element 1644 is shown where the walls of the adjustable element 1644 are folded in on themselves so that there are three or more portions of the wall adjacent to each other. Folding the walls of the adjustable element 1644 allows for the size of the adjustable element 1644 to be reduced. This in turn can allow for the size of the sheath 1640 to be reduced. In an additional embodiment, the folding the of the adjustable element can also assist in deploying the implantable device 1640 from the sheath 1604. In one embodiment, as the adjustable element 1644 is inflated a first portion 1670 (shown encircled in a broken line) of the adjustable element 1644 emerges through the slot 1638 (FIG. 16C). As the adjustable element 1644 continues to inflate, the first portion 1670 grows in size to become larger than the slot 1638. As further fluid is passed into the adjustable element 1644, the walls of the adjustable element 1644 begin to force the adjustable element 1644 completely through the slot 1638 (FIG. 16D). Once the adjustable element 1644 has passed through the slot 1638 the sheath 1604 can then be removed.

Figure 17:
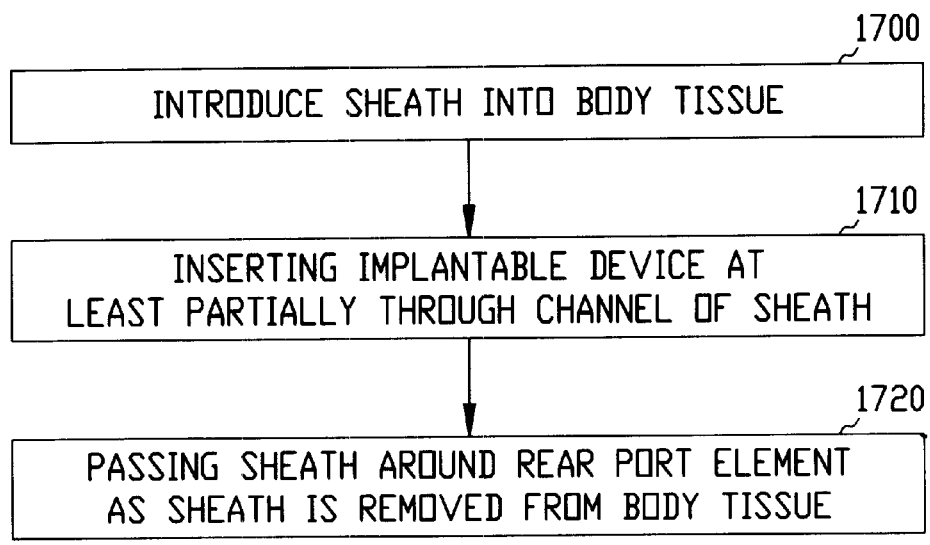
FIG. 17 is a method according to one embodiment of the present subject matter.

Referring now to FIG. 17, there is shown one embodiment of a method for adjustably restricting a body lumen according to the present subject matter. The implantable device assembly previously discussed is adapted to be surgically implanted into body tissue of a patient adjacent to a body lumen for coaptating the body lumen. At 1700, a sheath in introduced into body tissue of a patient. In one embodiment, the sheath is as previously described, where the sheath is introduced by first placing an obturator, or a dilator, having an end suitable for penetrating tissue through the channel of the sheath. Once the body lumen, such as the urethra, is located a small incision is made in the skin and the obturator is used to introduce the sheath into the body tissue to a desired location adjacent the urethra. This procedure is usually carried out under a local anesthetic with visual guidance, for instance under fluoroscopy by a physician. The obturator is of sufficient strength and rigidity to allow the insertion of the sheath into the tissue of the patient adjacent and parallel with the urethra.

In one embodiment, the sheath is inserted near the meatus urinarius and advanced through the periurethral tissue adjacent the urethra. In one embodiment, a detent or mark is provided on the sheath to ensure that the sheath is appropriately placed at the correct depth in the patient's body tissue. In an additional embodiment, the elongate body of the implantable medical device is available having a variety of lengths to accommodate the patient's anatomic structure so as to facilitate placement of the rear port element near the patient's skin. In one embodiment, the tubular elongate body of the implantable device once inserted into the patient's tissue can be cut to length prior to attaching the rear port element.

As previously described, the sheath includes a channel having a longitudinal axis and one or more dimensions perpendicular to the longitudinal axis. An example of the one or more dimensions includes a diameter of the channel, where the channel has a circular cross-section. Alternatively, the channel may have an elliptical cross-section, where the dimensions then have a major and a minor axis which define the ellipse.

At 1710, an implantable device is inserted at least partially through the channel of the sheath. In one embodiment, the implantable device includes an adjustable element, a tubular elongate body and a rear port element, as were previously described. In the present embodiment, the rear port element further includes at least one dimension that is larger than the one or more dimensions of the sheath. Examples of these were noted in the figures and the discussion for FIGS. 5 to 12 of the present subject matter. By way of example, at least one dimension that is larger than the one or more dimensions of the sheath can include the diameter of the outer surface of the rear port element and the inner diameter of the sheath. In this situation, the implantable device would not pass through the channel of the sheath as the diameter of the rear port element is larger than the diameter of the sheath.

The implantable medical device is advanced or moved at least partially though the channel to position the adjustable element distal to the sheath and adjacent the body lumen to be restricted. In one embodiment, the adjustable element is positioned adjacent an urethra. In an additional embodiment, two or more of the implantable medical devices can be implanted within the body tissue adjacent an urethra. The adjustable element is then expanded, or inflated, so as to retain the implantable medical device prior to removing the sheath.

At 1720, the sheath is then passed around the rear port element as the sheath is removed from the body tissue. In one embodiment, this is accomplished by splitting the sheath into one or more pieces as previously described. One manner of providing a sheath that will spilt is to create one or more scores on the sheath as previously described. The scores in the wall of the sheath provide lines of weakness, where the sheath can be torn along these one or more scores to allow the sheath to be passed around the rear port element as the sheath is removed from the body tissue.

In an additional embodiment, the sheath can have a slit as previously described, where the sheath is made of a material having the flexibility to allow the sheath to pass around the rear port element by passing the elongate body of the implantable device through the slit as the sheath is removed from the body tissue. Alternatively, the sheath can have a slot as previously described, where the sleeve is made of a material having a stiffness that requires the tubular elongate body of the implantable device to deform as it passes through the slot as the sheath is removed from the body tissue. The rear port element is then position subcutaneously.

After the implantable medical device has been implanted so the adjustable element (in its contracted state) is in the desired position adjacent to the urethra, the urethra is restricted to a desired degree by piercing the elastic septum of the rear port with a needle of a syringe and injecting a flowable material through the first interior passageway into the adjustable element. The physician may determine the desired degree of restriction of the urethra by means such as infusing fluid through the urethra past the restriction and measuring the back pressure or visually assessing the amount of coaptation of the urethra lumen after inflation of the adjustable element by use of cystoscopy. The flowable material may be, for example, a saline solution, a flowable gel, or a slurry of particles in a liquid carrier. It may be advantageous to make the flowable material radiopaque so that the degree of membrane inflation may be viewed by x-ray.

Figure 18:
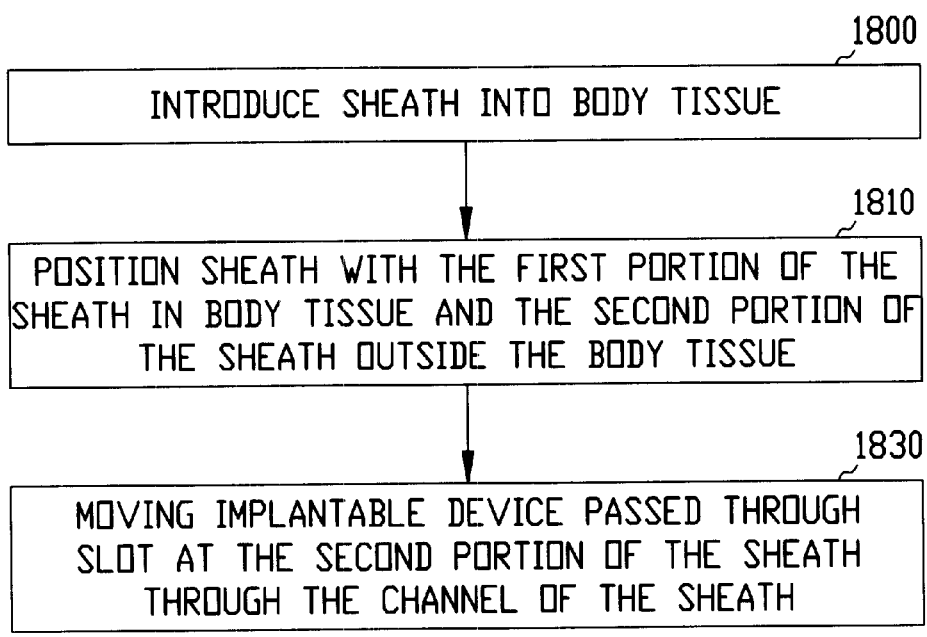
FIG. 18 is a method according to one embodiment of the present subject matter.

Referring now to FIG. 18, there is shown an additional embodiment of a method for adjustably restricting a body lumen according to the present subject matter. The implantable device assembly previously discussed is adapted to be surgically implanted into body tissue of a patient adjacent to a body lumen for coaptating the body lumen. At 1800, a sheath is introduced into body tissue of a patient, for example as previously described. In one embodiment, the sheath includes a first portion and a second portion, where at least the first portion of the sheath is introduced into the body tissue. In one embodiment, the sheath is introduced into the body tissue with a dilator, or obturator, which is inserted through the channel of the sheath.

Figure 19:
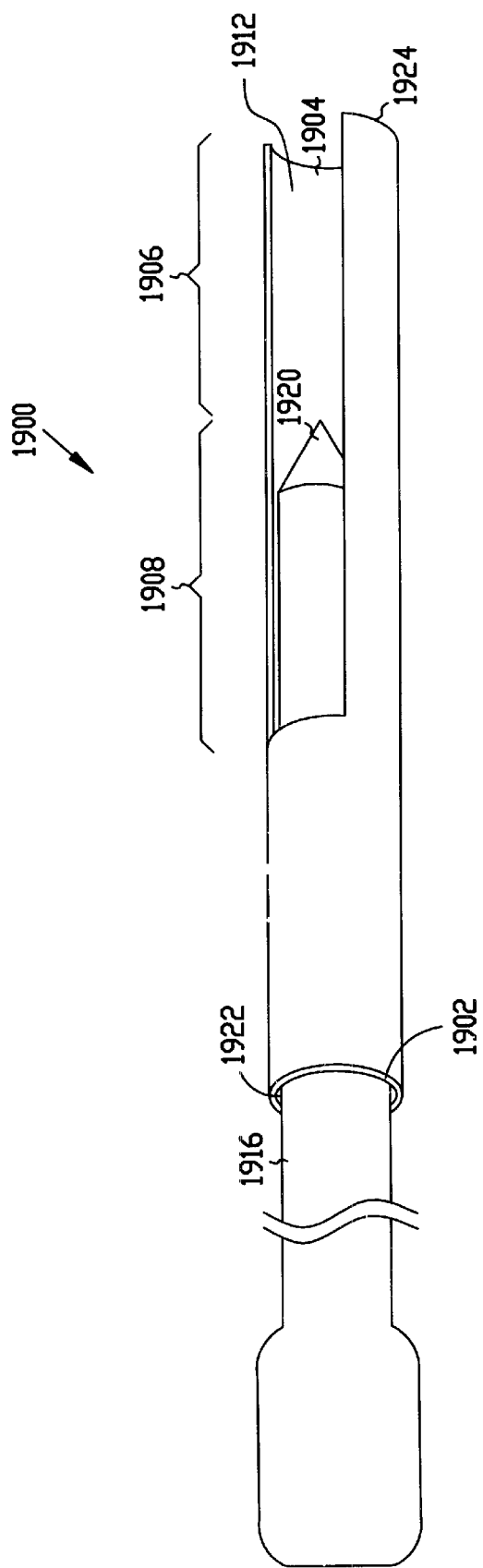
FIG. 19 is a schematic of an implantable device according to one embodiment of the present subject matter.

Referring now to FIG. 19, there is shown one embodiment of a sheath 1900, where the sheath 1900 includes a wall 1902 defining a channel 1904 having a longitudinal axis. The sheath 1900 further includes a first portion 1906, a second portion 1908, and a slot 1912 which extends longitudinally along a wall. In one embodiment, the first portion 1906 and the second portion 1908 include the portion of the sheath 1900 that includes the slot 1912. In an additional embodiment, a dilator 1916 is shown positioned in the channel 1904 of the sheath 1900. In one embodiment, the dilator 1916 includes a tip 1920 which is suitable for insertion into body tissue. The tip 1920 of the dilator 1916 is inserted into the channel 1904 at the proximal end 1922 of the channel 1904 and is slid, or moved, through the channel 1904 so that the tip 1920 extends from the distal end 1924 of the sheath 1900. The sheath 1900 and dilator 1916 are then inserted into the body tissue.

Referring again to FIG. 18, the sheath is positioned with the first portion of the sheath in body tissue and a second portion of the sheath outside the body tissue at 1810. In one embodiment, the second portion of the sheath includes at least a portion of the slot. At 1820, at least a portion of the implantable device is then moved through the channel of the sheath into the first portion of the sheath located in the body tissue. In one embodiment, at least a portion of the implanted device is positioned, or passed, through the slot at the second position.

Figure 20:
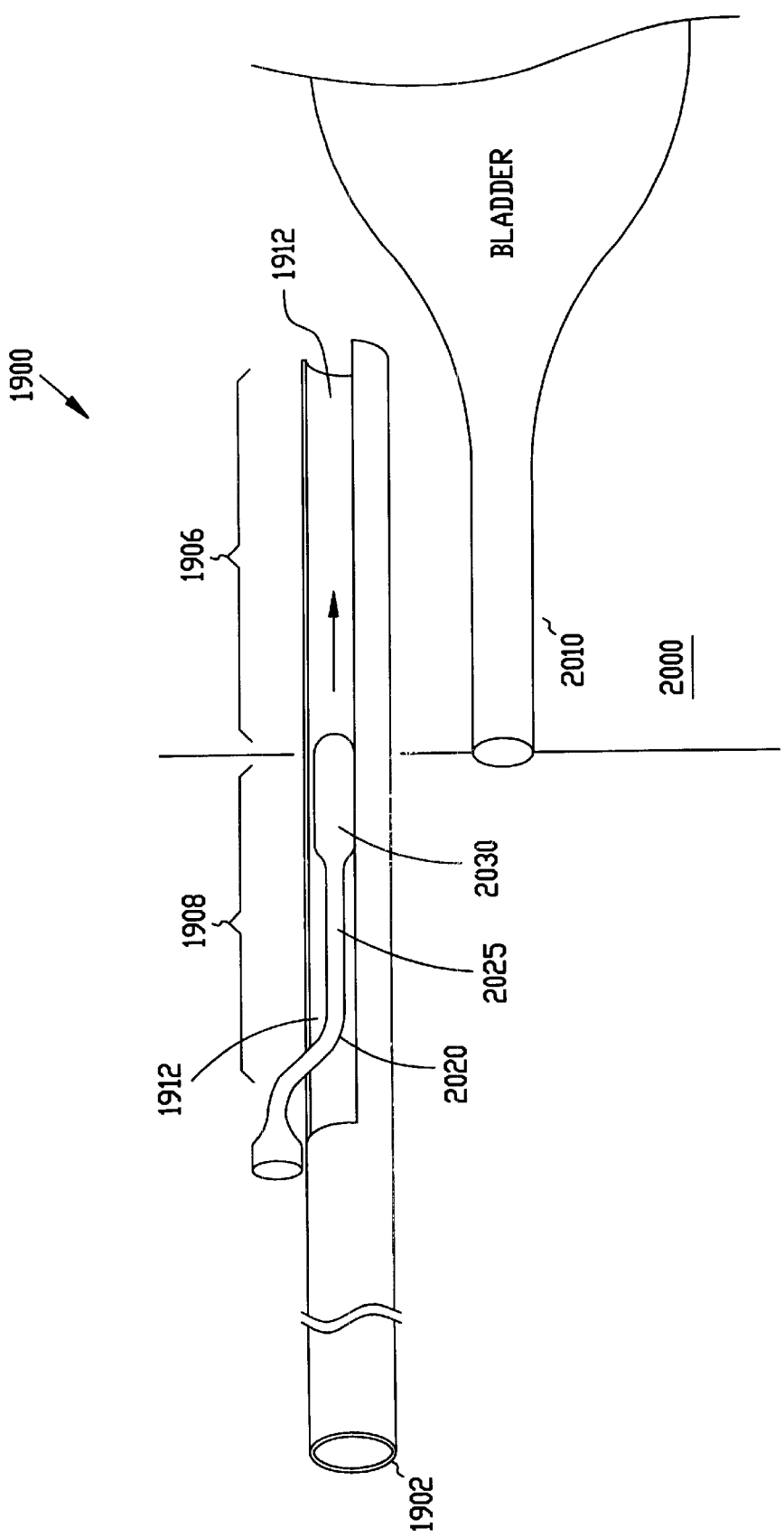
FIG. 20 is a schematic of an implantable device according to one embodiment of the present subject matter.

Referring now to FIG. 20, there is shown one embodiment of a sheath 1900 positioned within body tissue 2000. In one embodiment, the sheath is inserted near the meatus urinarius and advanced through the periurethral tissue adjacent the urethra 2010. In one embodiment, a detent or mark is provided on the sheath to ensure that the sheath is appropriately placed at the correct depth in the patient's body tissue. In one embodiment, the sheath 1900 is inserted into the body tissue so that the first portion 1906 is located within the body tissue and the second portion 1908 is not located within the body tissue. An implantable medical device 2020 is then positioned within the channel through the slot 1912.

The implantable medical device 2020 is then advanced, or moved, through the channel 1912 of the sheath 1900. In one embodiment, the implantable device is moved through the channel 1912 by inserting a rod having a distal end into the channel 1904 of the sheath 1900 until the distal end contacts implantable device 2020. Force is then applied to the distal end of the rod to move the implanted device 2020 at least partially through the channel 1912 of the sheath. Alternatively, the dilator could be used to move the implantable device through the channel 1912.

In an alternative embodiment, in order to move the implantable device 2020 the device is pushed towards the distal end of the sheath. In one embodiment, the implantable device 2020 includes an interior passage way, such as a second interior passageway previously described, where the interior passage way includes a first opening into which a push rod can be inserted until it contacts a closed end of the interior passage way which is distal to the first opening. Force can then be applied to the push rod to move the implanted device at least partially through the channel of the sheath. Alternatively, moving at least a portion of an implantable device includes positioning a sleeve, as previously described around at least a portion of the implantable device. In one embodiment, the sleeve is positioned around the tubular elongate body as previously described. Force is then applied to the sleeve to move the implanted device at least partially through the channel of the sheath. Alternatively, the tubular elongate body 2025 includes a support member, such as a coil located within the tubular elongate body as previously described, and pushing the implantable device includes applying force through the support member to move the implanted device at least partially through the channel of the sheath to position the adjustable element beyond the distal end of the sheath. In one embodiment, the adjustable element 2030 of the implantable device 2020 is moved through the channel to position the adjustable element 2030 beyond the distal end of the sheath 1900. Flowable material can then be introduced into the adjustable element to restrict a body lumen as previously discussed.

One feature of this invention relates to the adjustability of the adjustable element postoperatively. This adjustability is effected because the elastic septum is located remote from the adjustable element but near and under the patient's skin. The rear port element and the elastic septum are located by, for instance, manual palpation of the skin region and the needle of the syringe is inserted through the skin and septum so as to add or remove material from the adjustable element, thus increasing or decreasing the restriction of the body lumen.

In an additional embodiment, the rear port element can have any number of shapes that is more easily identifiable in the tissue during palpation by a physician. For example, the rear port element can have a oval cross-sectional shape. Alternatively, the rear port element can have a square cross-sectional shape. Other cross-sectional shapes can be imagined which would assist a physician in locating the rear port element. Additionally, the elastic septum of the rear port element can be positioned at a level that is higher (e.g., domed or bulbous), or lower, than that rear port element wall surrounding the elastic septum. This configuration assists the physician in finding the elastic septum quickly as it is set apart from the remainder of the rear port element. The rear port element can then be utilized for performing postoperative adjustments (e.g., days, weeks, months, years) of the size of the adjustable element.

We claim:

1. An implantable device assembly comprising:
   an implantable device including an adjustable element and a tubular elongate body, wherein the adjustable element includes a continuous wall, including an inner surface defining a chamber, and the tubular elongate body includes a peripheral surface, a proximal end and a distal end, where the peripheral surface is connected to and sealed to the adjustable element, the tubular elongate body including a first interior passageway which extends longitudinally in the tubular elongate body from a first opening at the proximal end to a second opening in fluid communication with the chamber of the implantable device for adjustably expanding or contracting the adjustable element by applied flowable material introduced through the first opening, the implantable device being adapted for implantation within a body for controllable coaptation of a lumen;
   a sleeve, where the sleeve includes a wall having an inner surface which is positioned adjacent the implantable device; and
   a sheath adapted to accommodate at least a portion of the implant device.

2. The implantable device assembly of claim 1, where the sleeve includes an outer surface, where the outer surface defines an arc which includes a first dimension that permits the sleeve to move longitudinally within the channel of the sheath, and the inner surface includes a second dimension which defines a volume that permits the tubular elongate body and the adjustable element to fit in the volume defined by inner surface of the sleeve.

3. The implantable device assembly of claim 2, where the sleeve includes a slot which extends longitudinally along the wall of the sleeve.

4. The implantable device assembly of claim 1, where the inner surface of the sleeve defines an arc with an inner diameter which permits at least a portion of the sleeve to be positioned around the peripheral surface of the tubular elongate body.

5. The implantable device assembly of claim 4, where the sleeve includes a slot which extends longitudinally along the wall of the sleeve.

6. The implantable device assembly of claim 4, where the sleeve includes a proximal and a distal end, where the distal end abuts a portion of the adjustable element and where the sleeve has a stiffness sufficient to allow force applied at the proximal end of the sleeve to move the implantable device at least partially through the channel of the sheath.

7. The implantable device assembly of claim 6, including a rear port element coupled to the proximal end of the tubular elongate body, the rear port element including a cavity in fluid communication with the first opening of the first interior passageway.

8. The implantable device assembly of claim 7, where the inner surface of the sleeve further defines receptacle region which has a shape and a size to receive at least a portion of the rear port element, where the receptacle region is positioned between the proximal and the distal end of the sleeve.

9. The implantable device assembly of claim 8, where the sheath includes a first portion and at least a second portion, where the second portion is of a lesser strength compared to the first portion and the second portion extends longitudinally along the wall to allow for the wall of the sheath to be separated.

10. The implantable device assembly of claim 9, where the second portion of the wall includes scorings extending longitudinally along the wall.

11. The implantable device assembly of claim 10, where the wall of the sheath includes two scorings extending longitudinally along the wall to allow for the sheath to be separated into two pieces.

12. The implantable device assembly of claim 8, where the sheath includes a slit through the wall, where the slit extends longitudinally along the wall.

13. The implantable device assembly of claim 7, including a flowable material source adapted to be releasably connected to the rear port element, where the adjustable element expands or contracts due to a volume of flowable material introduced into the cavity of the rear port element from the flowable material source to at least partially and adjustably restrict the body lumen.

14. The implantable device assembly of claim 7, where the rear port element is releasably coupled to the proximal end of the tubular elongate body.

15. The implantable device assembly of claim 1, where the tubular elongate body has a stiffness sufficient to allow force applied at the proximal end of the tubular elongate body to move the implantable device at least partially through the channel of the sheath.

16. The implantable device assembly of claim 15, where the tubular elongate body further includes a coil extending longitudinally through the tubular elongate body to impart the stiffness to the tubular elongate body and where the coil forms at least a portion of the first interior passageway.

17. An implantable device assembly comprising:
   an implantable device including an adjustable element and a tubular elongate body, wherein the adjustable element includes a continuous wall, including an inner surface defining a chamber, and the tubular elongate body includes a peripheral surface, a proximal end and a distal end, where the peripheral surface is connected to and sealed to the adjustable element, the tubular elongate body including a first interior passageway which extends longitudinally in the tubular elongate body from a first opening at the proximal end to a second opening in fluid communication with the chamber of the implantable device for adjustably expanding or contracting the adjustable element by applied flowable material introduced through the first opening, the implantable device being adapted for implantation within a body for controllable coaptation of a lumen; and
   a sheath adapted to accommodate at least a portion of the implant device, where the sheath includes a slot which extends longitudinally along the wall.

18. The implantable device assembly of claim 17, including a layer, where the layer traverses the slot in the wall and where the layer is made of a material, where the layer includes a slit.

19. The implantable device assembly of claim 17, where the continuous wall of the adjustable element is folded to allow the adjustable element to fit within the channel of the sheath.

20. The implantable device assembly of claim 17, including a rear port element coupled to the proximal end of the tubular elongate body, the rear port element including a cavity in fluid communication with the first opening of the first interior passageway.

21. The implantable device assembly of claim 20, including a flowable material source adapted to be releasably connected to the rear port element, where the adjustable element expands or contracts due to a volume of flowable material introduced into the cavity of the rear port element from the flowable material source to at least partially and adjustably restrict the body lumen.

22. The implantable device assembly of claim 20, where the tubular elongate body includes a second interior passageway which extends longitudinally along at least a portion of the tubular elongate body from an inlet to a closed end, where the second interior passageway is of sufficient diameter to receive a push rod adapted to contact the closed end to allow force applied to the push rod to move the implanted device at least partially through the channel of the sheath.

23. The implantable device assembly of claim 20, where the tubular elongate body further includes a coil extending longitudinally through the tubular elongate body, where the coil forms at least a portion of the first interior passageway.

24. An implantable device assembly for controllable coaptation of a body lumen, comprising:
   an implantable device including an adjustable element and a tubular elongate body, wherein the adjustable element includes a continuous wall, including an inner surface defining a chamber, and the tubular elongate body includes a peripheral surface, a proximal end and a distal end, where the peripheral surface is connected to and sealed to the adjustable element, the tubular elongate body including a first interior passageway which extends longitudinally in the tubular elongate body from a first opening at the proximal end to a second opening in fluid communication with the chamber of the implantable device for adjustably expanding or contracting the adjustable element by applied flowable material introduced through the first opening; and
   a tip attached to the implantable device, the tip suitable to penetrate tissue, where the adjustable element expands under pressure from a volume of flowable material introduced through the first opening to at least partially envelop the tip.

25. The implantable device assembly of claim 24, where the distal end of the tubular body forms the tip.

26. The implantable device assembly of claim 24, where the first interior passageway is of sufficient diameter to receive and guide a push rod adapted to contact a closed end to allow force applied to the push rod to move the implanted device at least partially through the tissue.

27. The implantable device assembly of claim 24, including a rear port element coupled to the proximal end of the tubular elongate body, the rear port element including a cavity in fluid communication with the first opening of the first interior passageway.

28. The implantable device assembly of claim 27, including a flowable material source adapted to be releasably connected to the rear port element, where the adjustable element expands or contracts due to a volume of flowable material introduced into the cavity of the rear port element from the flowable material source to at least partially and adjustably restrict the body lumen.

29. A method for implanting an implantable device, comprising:
   introducing at least a first portion of a sheath into body tissue, where the sheath includes a wall defining a channel, and a slot which extends longitudinally along the wall;
   positioning the sheath with the first portion of the sheath in body tissue and a second portion of the sheath outside the body tissue, where the second portion of the sheath includes at least a portion of the slot; and
   moving at least a portion of the implantable device passed through the slot located in the second portion of the sheath through the channel of the sheath into the first portion of the sheath located in the body tissue.

30. The method of claim 29, where introducing at least the first portion of the sheath includes positioning a dilator in the channel of the sheath, where the dilator has a tip suitable to penetrate body tissue.

31. The method of claim 30, where moving the implantable device includes inserting a rod having a distal end into the channel of the sheath until the distal end contacts implantable device; and
   applying force to the rod to move the implanted device at least partially through the channel of the sheath.

32. The method of claim 29, where the sheath includes a distal end and a proximal end, and where the slot extends from the distal end to a position between the proximal end and the distal end, and where moving at least a portion of an implantable device includes pushing the implantable device towards the distal end of the sheath.

33. The method of claim 29, where moving at least a portion of an implantable device includes inserting a push rod into an interior passageway of the implantable device through a first opening until the push rod contacts a closed end distal to the first opening; and applying force to the push rod to move the implanted device at least partially through the channel of the sheath.

34. The method of claim 29, where moving at least a portion of an implantable device includes positioning a sleeve around at least a portion of the implantable device, and applying force to the sleeve to move the implanted device at least partially through the channel of the sheath.

35. The method of claim 32, where the implantable device includes a rear port element, a tubular elongate body, and an adjustable element, where the tubular elongate body includes a support member and pushing the implantable device includes applying force through the support member to move the implanted device at least partially through the channel of the sheath to position the adjustable element beyond the distal end of the sheath.

36. The method of claim 29, where the sheath includes a distal end and the implantable device includes an adjustable element, and where moving the implantable device through the channel includes positioning the adjustable element beyond the distal end of the sheath.

37. The method of claim 36, including introducing flowable material into the adjustable element to restrict a body lumen.

* * * * *